(12) United States Patent
Armitstead et al.

(10) Patent No.: US 10,342,939 B2
(45) Date of Patent: Jul. 9, 2019

(54) DETECTION OF VENTILATION SUFFICIENCY

(75) Inventors: Jeffrey Peter Armitstead, North Sydney (AU); Dinesh Ramanan, Telopea (AU)

(73) Assignee: ResMed Pty Ltd (AU)

( * ) Notice: Subject to any disclaimer, the term of this patent is extended or adjusted under 35 U.S.C. 154(b) by 1156 days.

(21) Appl. No.: 14/006,772

(22) PCT Filed: Mar. 15, 2012

(86) PCT No.: PCT/AU2012/000270
§ 371 (c)(1),
(2), (4) Date: Sep. 23, 2013

(87) PCT Pub. No.: WO2012/126041
PCT Pub. Date: Sep. 27, 2012

(65) Prior Publication Data
US 2014/0007878 A1 Jan. 9, 2014

Related U.S. Application Data

(60) Provisional application No. 61/466,560, filed on Mar. 23, 2011.

(51) Int. Cl.
*A61M 16/00* (2006.01)
*A61B 5/083* (2006.01)
(Continued)

(52) U.S. Cl.
CPC ......... *A61M 16/0051* (2013.01); *A61B 5/083* (2013.01); *A61B 5/087* (2013.01);
(Continued)

(58) Field of Classification Search
CPC ....... A61B 5/083; A61B 5/087; A61B 5/7264; A61M 2016/0027; A61M 2016/0039;
(Continued)

(56) References Cited

U.S. PATENT DOCUMENTS 5,335,654 A 8/1994 Rapoport
5,704,345 A 1/1998 Berthon-Jones
(Continued)

FOREIGN PATENT DOCUMENTS

JP 2004506499 A 3/2004
JP 2008514379 A 5/2008
WO 03030804 A2 4/2003

OTHER PUBLICATIONS

Berry, Richard B. et al. "Rules for Scoring Respiratory Events in Sleep: Update of the 2007 AASM Manual for the Scoring of Sleep and Associated Events: Deliberations of the Sleep Apnea Definitions Task Force of the American Academy of Sleep Medicine." Journal of Clinical Sleep Medicine, https://www.ncbi.nlm.nih.gov/pmc/articles/PMC3459210/.*
(Continued)

*Primary Examiner* — Jan Christopher L Merene
*Assistant Examiner* — Joseph D. Boecker
(74) *Attorney, Agent, or Firm* — Botos Churchill IP Law LLP

(57) ABSTRACT

Automated methods provide a ventilation sufficiency assessment to evaluate patient respiration. In some embodiments, a ventilation histogram maybe determined from a measure of patient respiratory flow. Based on the histogram or associated ventilation data, hypoventilation or hyperventilation occurrences may be detected. For example, a kurtosis index and/or skewness index may be calculated with the data associated with the ventilation histogram and may be evaluated as an indication of hypoventilation or hyperventilation. An assessment of the number of peaks and other features of the ventilation histogram, such as in the case of a bimodal ventilation histogram, may be implemented to detect an occurrence of ventilation insufficiency or sufficiency. The detection methodologies may be implemented by a specific purpose computer, a detection device that measures a respi-
(Continued)

ratory airflow or a respiratory treatment apparatus that provides a respiratory treatment regime based on the detected ventilation sufficiency.

62 Claims, 17 Drawing Sheets

(51) Int. Cl.
*A61B 5/087* (2006.01)
*A61B 5/00* (2006.01)

(52) U.S. Cl.
CPC .... *A61M 16/0057* (2013.01); *A61M 16/0069* (2014.02); *A61B 5/7264* (2013.01); *A61M 2016/0027* (2013.01); *A61M 2016/0039* (2013.01); *A61M 2205/15* (2013.01); *A61M 2205/18* (2013.01); *A61M 2205/3553* (2013.01); *A61M 2205/502* (2013.01); *A61M 2230/435* (2013.01)

(58) Field of Classification Search
CPC .......... A61M 16/0051; A61M 16/0057; A61M 16/0069; A61M 2205/15; A61M 2205/18; A61M 2205/3553; A61M 2205/502; A61M 2230/435
See application file for complete search history.

(56) References Cited

U.S. PATENT DOCUMENTS

| | | | |
|---|---|---|---|
| 6,099,481 A * | 8/2000 | Daniels ................ | A61B 5/083 128/204.23 |
| 6,273,088 B1 | 8/2001 | Hillsman | |
| 6,752,766 B2 * | 6/2004 | Kowallik .......... | A61M 16/0051 128/204.23 |
| 6,881,192 B1 * | 4/2005 | Park ................... | A61N 1/36585 600/484 |
| 7,717,110 B2 * | 5/2010 | Kane .................... | A61M 16/00 128/204.21 |
| 2001/0039950 A1 * | 11/2001 | Scholler .............. | A61B 5/0816 128/204.18 |
| 2004/0111014 A1 * | 6/2004 | Hickle ................ | A61B 5/0002 600/300 |
| 2005/0085865 A1 * | 4/2005 | Tehrani ............... | A61N 1/3601 607/42 |
| 2006/0000475 A1 * | 1/2006 | Matthews ......... | A61M 16/0051 128/204.21 |
| 2006/0070624 A1 * | 4/2006 | Kane .................... | A61M 16/00 128/204.23 |
| 2006/0282002 A1 | 12/2006 | Wang et al. | |
| 2007/0073181 A1 | 3/2007 | Pu et al. | |
| 2007/0084464 A1 | 4/2007 | Wickham et al. | |
| 2007/0129645 A1 | 6/2007 | Hartley et al. | |
| 2007/0163590 A1 * | 7/2007 | Bassin ................. | A61M 16/00 128/204.23 |
| 2007/0221224 A1 * | 9/2007 | Pittman ............. | A61M 16/0051 128/204.22 |
| 2008/0269583 A1 * | 10/2008 | Reisfeld ............... | A61B 5/0205 600/364 |

OTHER PUBLICATIONS

International Search Report and Written Opinion for Application No. PCT/AU2012/00270 dated May 18, 2012.

European Search Report for Application No. 12761355.2 dated Oct. 13, 2014.

* cited by examiner

DETECTION OF VENTILATION SUFFICIENCY

CROSS REFERENCE TO RELATED APPLICATIONS

The present application is a national phase entry under 35 U.S.C. § 371 of International Application No. PCT/AU2012/000270 filed Mar. 15, 2012, published in English, which claims priority from U.S. Provisional Patent Application No. 61/466,560 filed Mar. 23, 2011, all of which are incorporated herein by reference.

FIELD OF THE TECHNOLOGY

The present technology relates to methods and apparatus for detection of respiratory ventilation sufficiency or insufficiency, such as normal patient ventilation, hyperventilation or hypoventilation.

BACKGROUND OF THE TECHNOLOGY

A form of pressure treatment, typically for patients with obstructive sleep apnea (OSA), is continuous positive airway pressure (CPAP) applied by a blower (compressor) via a connecting hose and mask. The positive pressure may be used to prevent collapse of the patient's airway during inspiration, thus preventing recurrent apnoeas or hypopnoeas and their sequelae. Such a respiratory treatment apparatus can function to generate a supply of clean breathable gas (usually air, with or without supplemental oxygen) at the therapeutic pressure or pressures that may change to treat different events but may remain approximately constant across a given cycle of the patient respiration cycle (i.e., inspiration and expiration) or may be reduced for comfort during each expiration (e.g., bi-level CPAP).

Respiratory treatment apparatus can typically include a flow generator, an air filter, a mask or cannula, an air delivery conduit connecting the flow generator to the mask, various sensors and a microprocessor-based controller. The flow generator may include a servo-controlled motor and an impeller. The flow generator may also include a valve capable of discharging air to atmosphere as a means for altering the pressure delivered to the patient as an alternative to motor speed control. The sensors measure, amongst other things, motor speed, gas volumetric flow rate and outlet pressure, such as with a pressure transducer, flow sensor or the like. The apparatus may optionally include a humidifier and/or heater elements in the path of the air delivery circuit. The controller may include data storage capacity with or without integrated data retrieval/transfer and display functions.

In addition to apnoeas or hypopnoeas, patients on pressure treatment therapy, such as CPAP therapy, might also experience hypoventilation. Hypoventilation may be considered an occurrence of a persistently low ventilation as opposed to a periodic pause or apnoea. Such incidents of hypoventilation may not be recorded or recognized by the patient or by a clinician or physician managing the patient.

In a case of the patient receiving CPAP therapy, hypoventilation may present for a number of reasons:

(a) The patient may have a primary diagnosis of obesity hypoventilation syndrome (OHS) and CPAP is being trialed as a therapy. Many patients recover over months with such treatment. Although overnight oxygen blood saturation ($SpO_2$) recording is the standard way of identifying efficacy, this is potentially costly and cumbersome.

(b) The patient may develop hypoventilation over time due to an underlying disease process (e.g., chronic obstructive pulmonary disease (COPD) progression or OHS progression from obstructive sleep apnea (OSA)).

(c) The patient may have had a limited diagnostic test where the hypoventilation was missed Dr, for example, they did not enter the sleep state where hypoventilation presents (e.g., supine sleep).

It may be desirable to develop methods for evaluating or accessing patient ventilation, which may also be implemented in apparatus for assessment of ventilation or apparatus for generating a respiratory pressure treatment.

SUMMARY OF THE TECHNOLOGY

A first aspect of some embodiments of the present technology is to provide methods and devices for assessing ventilation.

Another aspect of some embodiments of the technology is to determine a ventilation histogram in an apparatus based on a measure of respiratory flow from a flow sensor.

A still further aspect of the technology is to implement the detection of ventilation sufficiency in a respiratory treatment apparatus, such as a continuous positive airway pressure device, based on or as a function of a ventilation histogram.

Another aspect of the present technology is a method for detecting hypoventilation comprising the steps of: (i) determining a measure of flow; (ii) calculating a measure of ventilation from said measure of flow; (iii) determining a probability distribution of said measure of ventilation; and (iv) analyzing the probability distribution to detect hypoventilation.

Some embodiments of the technology involve a method for controlling a processor to assess sufficiency of ventilation from a measured flow of breathable gas. Such a method of the processor may include accessing a measure of a flow of breathable gas representative of patient respiration, deriving measures of ventilation from the measure of flow, and determining, with a processor, a histogram based on the measures of ventilation.

Such a method may also involve displaying a graph of the histogram on a visual display device. Optionally, the histogram may represent a frequency distribution of ventilation values taken over the course of a treatment session where each ventilation value is a measure of volume over a time interval. The time interval may be shorter than the time of the treatment session. Optionally, the time interval may be on an order of a minute and the time of the treatment session may be on an order of hours.

In some embodiments, the method may further involve processing, in the processor, data associated with the histogram to calculate a skewness index, comparing the skewness index to a threshold, and indicating hypoventilation or hyperventilation based on the comparison.

In some cases, the method may also include processing, in the processor, data associated with the histogram to detect a number of peaks of, the histogram, and indicating a presence or absence of hypoventilation based on the number of detected peaks.

In still further cases, method may also include processing, in the processor, data associated with the histogram to determine a kurtosis index, comparing the kurtosis index to a threshold, and indicating a presence or absence of hypoventilation based on the comparison.

Optionally, such a method may further include controlling, with the processor, measuring of the flow of breathable gas with a flow sensor.

In some cases, the method may include processing data representing the histogram to generate a hypoventilation indicator where the indicator represents an occurrence of an event of hypoventilation. Optionally, the hypoventilation indicator may include a probability value. The processing may include a detection of peaks of the histogram. The processing may also include calculating a distance between peaks of the histogram and transforming the distance into a probability space. The processing may also include calculating a gradient between peaks of the histogram. The processing may also include calculating an area with respect to the gradient and transforming the area into a probability space. The processing may also include calculating a set of features of the histogram and generating the indicator based on an, evaluation of the set of features. The set of features may include one or more of the following features: a gradient between two largest peaks, a gradient between a largest peak and a center point, a gradient between a second largest peak and a center point, an area between two largest peaks, an area between a largest peak and a center point, an area between a second largest peak and a center point, a shape feature, kurtosis value and skewness value.

In some such cases, the method may further involve determining a measure of leak and distinguishing measures of ventilation for the histogram based on the measure of leak, such as by partitioning a histogram for display accordingly and/or by disregarding ventilation measures corresponding to periods of leak. In still further cases, the method may involve determining a measure of ventilation stability and distinguishing measures of ventilation for the histogram based on the measure of stability, such as by partitioning a histogram for display accordingly and/or by disregarding ventilation measures corresponding to periods of instability. In some such cases, the determining of the measure of ventilation stability may involve any of one or more of a detection of an awake period, an apnea event, a periodic breathing event and an arousal event.

Some embodiments of the present technology may include a ventilation assessment apparatus. The apparatus may typically include a controller having at least one processor to access data representing a measured flow of breathable gas attributable to patient respiration, the controller being further configured to (a) derive measures of ventilation from the measure of flow, and (b) determine a histogram based on the measures of ventilation.

In some such embodiments of the apparatus, the controller may be further configured to display a graph of the histogram on a visual display device. In such cases, the histogram may represent a frequency distribution of ventilation values taken over the course of a treatment session where each ventilation value may be a measure of volume over a time interval. The time interval may be shorter than the time of the treatment session. Optionally, the time interval may be on an order of a minute and the time of the treatment session is on an order of hours.

In some embodiments of the apparatus, the controller may also be configured to process data associated with the histogram to calculate a skewness index, to compare the skewness index to a threshold, and to indicate an occurrence of hypoventilation or hyperventilation based on the comparison.

Optionally, the controller may also be configured to process data associated with the histogram to detect a number of peaks of the histogram, and to indicate a presence or absence of hypoventilation based on the number of detected peaks. The controller may also be configured to process data associated with the histogram to determine a kurtosis index, to compare the kurtosis index to a threshold, and to indicate a presence or absence of hypoventilation based on the comparison.

In some such embodiments, the apparatus may also include a flow sensor, and the controller may also be configured to control measuring of the flow of breathable gas with the flow sensor.

Still further, the apparatus may also include a flow generator configured to produce a breathable gas for a patient at a pressure above atmospheric pressure. In such a case, the controller may also be configured to control the flow generator to produce the breathable gas according to a pressure therapy regime based on an assessment of any one or more of (a) the histogram, (b) a number of peaks of the histogram, (c) a kurtosis index determined from data associated with the histogram and (d) a skewness index determined from data associated with the histogram.

Optionally, the controller may be configured to process data representing the histogram to generate a hypoventilation indicator where the indicator represents an occurrence of an event of hypoventilation. The hypoventilation indicator may include a probability value. The controller may also be configured to detect peaks of the histogram. The controller may also be configured to calculate a distance between peaks of the histogram and transforming the distance into a probability space. The controller may be configured to calculate a gradient between peaks of the histogram. The controller may also be configured to calculate an area with respect to the gradient and transform the area into a probability space. In some cases, the controller may also be configured to calculate a set of features of the histogram and to generate the indicator based on an evaluation of the set of features. The set of features may include one or more of the following features: a gradient between two largest peaks, a gradient between a largest peak and a center point, a gradient between a second largest peak and a center point, an area between two largest peaks, an area between a largest peak and a center point, an area between a second largest peak and a center point, a shape feature, kurtosis value and skewness value.

Optionally, in some cases, the controller may be configured to determine a measure of leak and to distinguish the measures of ventilation for the histogram based on the measure of leak. Still further, the controller may be configured to determine a measure of ventilation stability and to distinguish the measures of ventilation for the histogram based on the measure of stability. The controller may determine the measure of ventilation stability by detecting any of one or more of an awake period, an apnea event, a periodic breathing event and an arousal event.

Another embodiment of the present technology may involve a ventilation assessment system. The system may include means for measuring a flow of breathable gas attributable to patient respiration during a treatment session, means for deriving measures of ventilation from the measure of flow, and means for determining a histogram based on the measures of ventilation.

Such a system may also include means for displaying a visual graph of the histogram. It may also include means for evaluating a skewness index based on data associated with the histogram to detect an occurrence of hypoventilation or hyperventilation. The system may also include means for evaluating a number of histogram peaks from data associated with the histogram to detect an occurrence of hypoventilation. It may also include means for evaluating a kurtosis index based on data associated with the histogram to detect a presence or absence of hypoventilation. In some embodiments, the system may also include means for generating a breathable gas for a patient at a pressure above atmospheric pressure based on an assessment of any one or more of (a) the histogram, (b) a number of peaks of the histogram, (c) a kurtosis index determined from data associated with the histogram and (d) a skewness index determined from data associated with the histogram.

The system may also include means for processing data representing the histogram to generate a hypoventilation indicator where the indicator represents an occurrence of an event of hypoventilation. The hypoventilation indicator may include a probability value. The system may also include means for detecting peaks of the histogram. The system may also include means for calculating a distance between peaks of the histogram and transforming the distance into a probability space. The system may also include means for calculating a gradient between peaks of the histogram. The system may also include means for calculating an area with respect to the gradient and transforming the area into a probability space. The system may also include means for calculating a set of features of the histogram and generating the indicator based on an evaluation of the set of features. The set of features may include one or more of the following features: a gradient between two largest peaks, a gradient between a largest peak and a center point, a gradient between a second largest peak and a center point, an area between two largest peaks, an area between a largest peak and a center point, an area between a second largest peak and a center point, a shape feature, kurtosis value and skewness value.

In some cases, the system may include a leak detector to determine a measure of leak. The system may be configured to distinguish the measures of ventilation for the histogram based on the measure of leak. Similarly, the system may include a ventilation stability detector. The system may be configured to distinguish the measures of ventilation for the histogram based on the measure of stability. In some such cases, the ventilation stability detector may include means for detecting any one or more of an awake period, an apnea event, a periodic breathing event and an arousal event.

Additional features of the present ventilation assessment technology will be apparent from a review of the following detailed discussion, drawings and claims.

BRIEF DESCRIPTION OF DRAWINGS

The present technology is illustrated by way of example, and not by way of limitation, in the figures of the accompanying drawings, in which like reference numerals refer to similar elements including.

DETAILED DESCRIPTION

Figure 1:
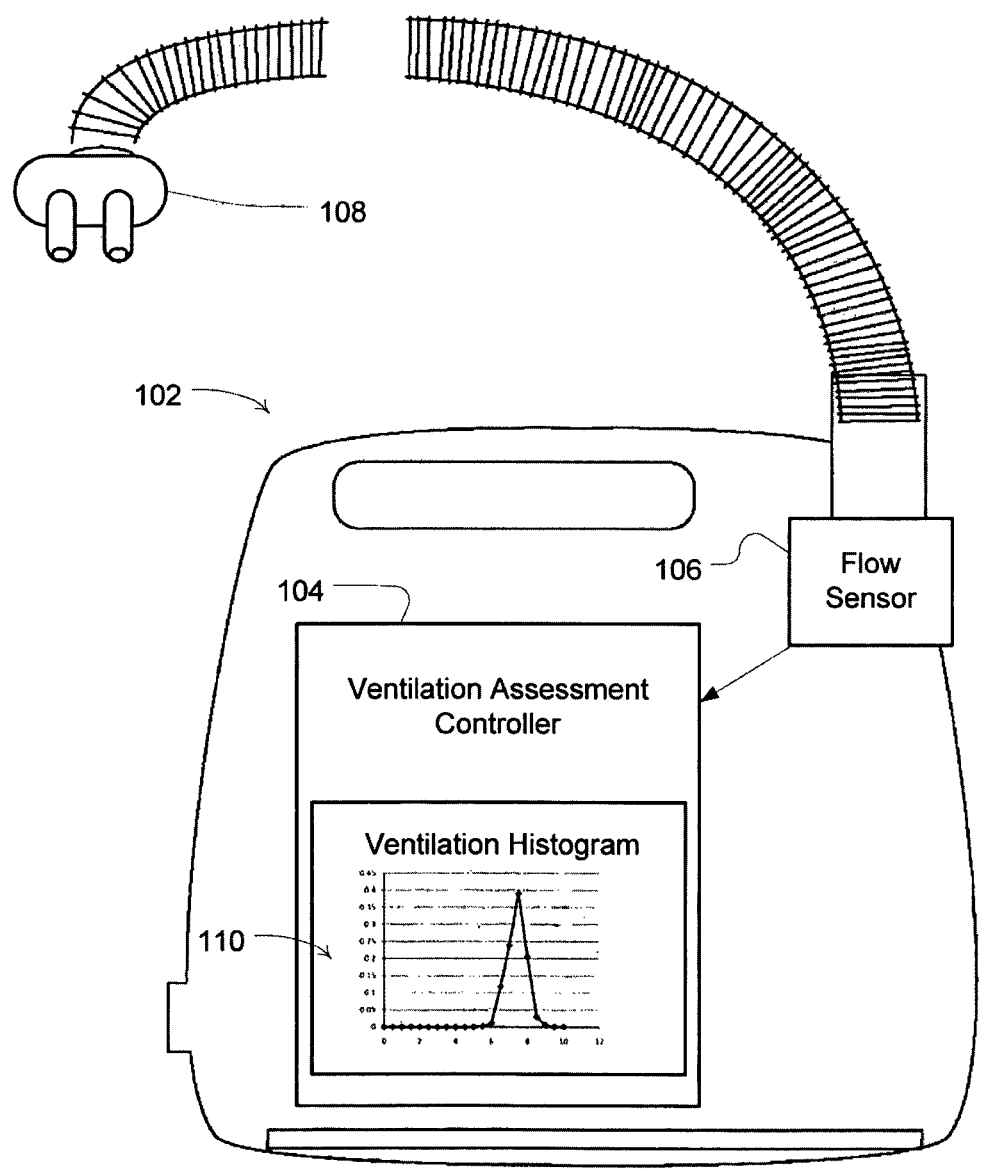
FIG. 1 shows an example ventilation assessment apparatus of the present technology with an optional flow sensor.

As illustrated in FIG. 1, embodiments of the present technology may include a ventilation assessment device 102 or apparatus having a controller 104 that may have one or more processors to implement particular ventilation assessment methodologies such as the algorithms described in more detail herein. In some such embodiments, the ventilation assessment may provide a determination of ventilation adequacy such as by determining an incident of hyperventilation or hypoventilation. The ventilation assessment may also optionally provide information for making such a determination such as by generating or analyzing a ventilation histogram. An example of a plotted ventilation histogram 110 is shown in FIG. 1. To these ends, the device or apparatus may include integrated chips, a memory and/or other control instruction, data or information storage medium. For example, programmed instructions encompassing the assessment methodologies may be coded on integrated chips in the memory of the device or apparatus to form an application specific integrated chip (ASIC). Such instructions may also or alternatively be loaded as software or firmware using an appropriate data storage medium.

With such a controller or processor, the device can be used for processing data from a flow signal. Thus, the Processor may control the assessment of patient ventilation as described in the embodiments discussed in more detail herein based on accessing measured and recorded respiratory flow data from a prior sleep session. Alternatively, the ventilation assessment may be performed during a sleep session contemporaneously with the measuring of a respiratory flow signal. Thus, in some embodiments, the device or apparatus itself may optionally be implemented with a flow sensor 106 for measuring a flow signal for use with the implemented methodologies. For example, flow to or through a nasal cannula 108 or mask may be measured using a pneumotachograph and differential pressure transducer or, similar device such as one employing a bundle of tubes or ducts to derive a flow signal. Optionally, a patient respiratory flow signal may be determined by subtracting estimated measures of vent flow and leak flow from the measure of total flow produced by a flow, sensor such as in the case that that flow sensor measures a flow of gas in addition to patient respiratory flow. Optionally, a flow signal may be inferred from other sensors, such as, a motor current sensor as described in PCT/AU2005/001688 filed on Nov. 2, 2005, and U.S. patent application Ser. No. 12/294,957, the National Stage thereof, the entire disclosures of which is incorporated herein by cross reference. Similarly, a flow signal may be generated by a non-contact sensor such as by a pulse radio frequency transceiver and signal processing of reflected pulse radio frequency signals or by an ultrasonic screening sensor. For example, the sensor may monitor sound such as by the use of ultrasonic sensors to detect respiratory parameters such as a respiratory flow signal from the signals measured by the sensors.

(A) Example Ventilation Assessment Features

Figure 2:
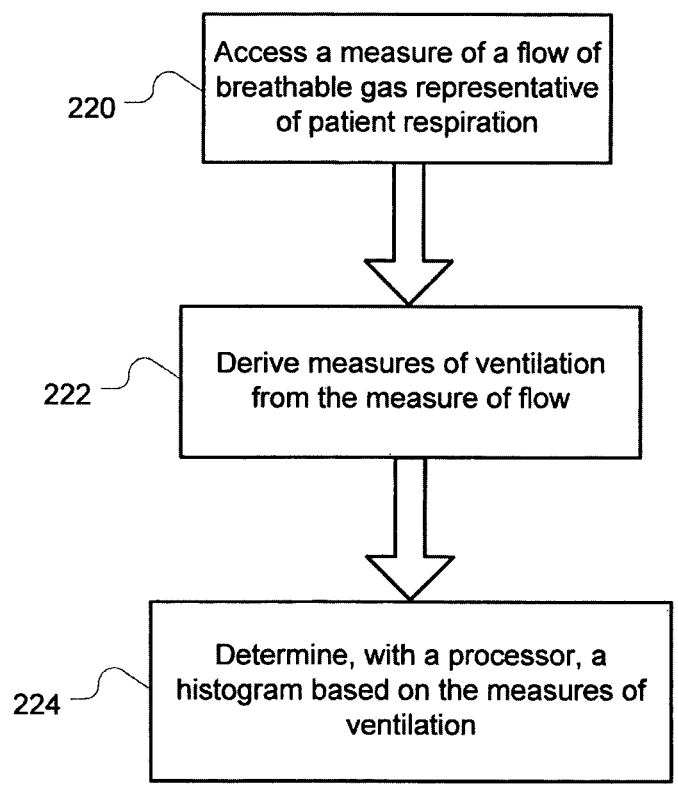
FIG. 2 is a flow diagram of an example embodiment of a method of controlling an apparatus to assess patient ventilation.

As illustrated in the flow chart of FIG. 2, in some embodiments of the present technology an automated assessment of ventilation by an assessment device may involve a determination or calculation of a ventilation histogram, which may be based on data representing a measure of a flow of breathable gas or a respiratory flow signal. For example, at 220 a controller or processor may access a measure of a flow of breathable gas representative of patient respiration that may be taken during the course of a treatment session, such as a night sleep or several hours of treatment. At 222, the controller or processor may then derive a measure of patient ventilation or measures of ventilation from the measure of flow. The measure of ventilation may typically be a signal representing a volume of air inspired or expired over a period of time. For example, such a measure may be determined as a low pass filtered absolute value of the respiratory flow. Such a low pass filter may be implemented with a time constant on the order of minutes. For example, it may be in the range of 60 to 200 seconds but preferably about 180 seconds. The measure may be partitioned or sampled to determine discrete measures from the ventilation signal. Optionally, each value of these measures of ventilation may be represented as a number of liters inspired or expired per minute (e.g., measures of minute ventilation). Alternatively, the measures of ventilation may be the measured tidal volume for each respiratory cycle during a treatment session, such as the liters per cycle.

At 224, a ventilation histogram may be determined based on the measures of ventilation by a processor. For example, a frequency distribution of the measures of ventilation taken over the course of a treatment session may be computed. For example, the determined ventilation values may be compared to discrete intervals (e.g., at or about a liter per minute) to determine how frequent all of the measured ventilation values are in the different intervals. Optionally, the ventilation histogram may be plotted such that the interval or intervals with a high frequency or greatest frequency (e.g., one or more peaks) may be observed. Similarly, the data associated therewith may be evaluated by a processor such that the interval or intervals with a high frequency or greatest frequency (e.g., one or more peaks) may be detected. Optionally, the data may also be evaluated to determine skewness and/or peakedness (e.g., kurtosis).

Optionally, the data associated with the ventilation histogram may also be evaluated to determine one or more of the following features: a shape feature of the ventilation histogram; the gradient of the line connecting the two largest peaks in the ventilation histogram; the gradient of the line connecting the highest peak and the center point of the ventilation histogram; the gradient of the line connecting the $2^{nd}$ highest peak and the center point of the ventilation histogram; the area below the center point and the highest peak of the ventilation histogram; the area below the center point and $2^{nd}$ highest peak of a ventilation histogram; the distance between the two highest peaks.

Such observations or evaluations may then optionally be utilized, either individually or in combination, to determine whether or not an incident of hypoventilation or hyperventilation has occurred. Thus, the ventilation assessment device, in addition to determining a ventilation histogram, may also score or record incidents of hypoventilation or hyperventilation. The scoring of such incidents may optionally include an identification of the derived ventilation values that are indicative of the hyperventilation or hypoventilation incident. Optionally, the scoring may also include an identification of a time or of one or more time periods during a treatment session when the incident occurred and/or the duration of the incident.

Figure 3:
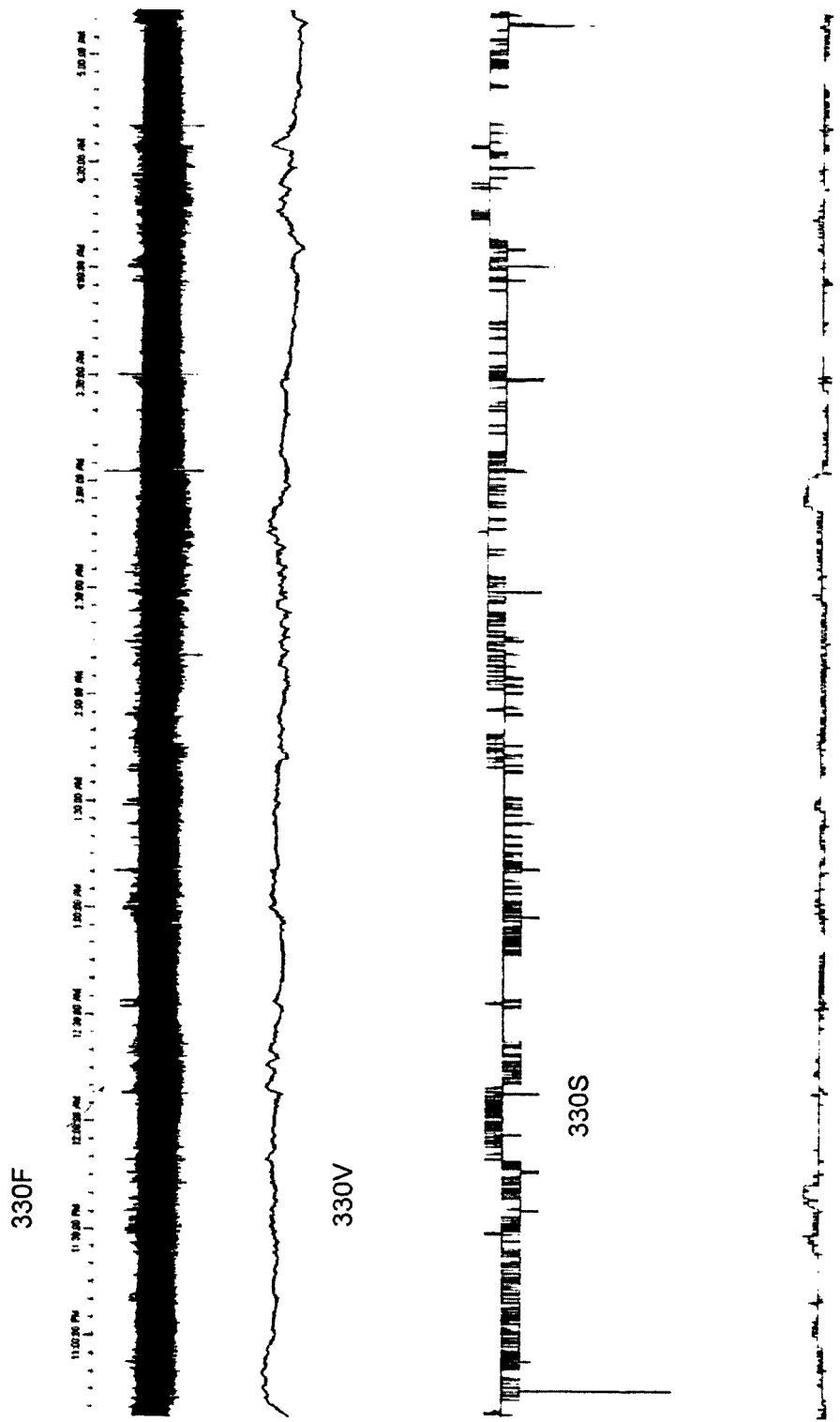
FIG. 3 is an example graph showing a plot of flow, ventilation, oxygen saturation and leak signals during the course of a night's treatment session with a respiratory treatment apparatus.
Figure 4:
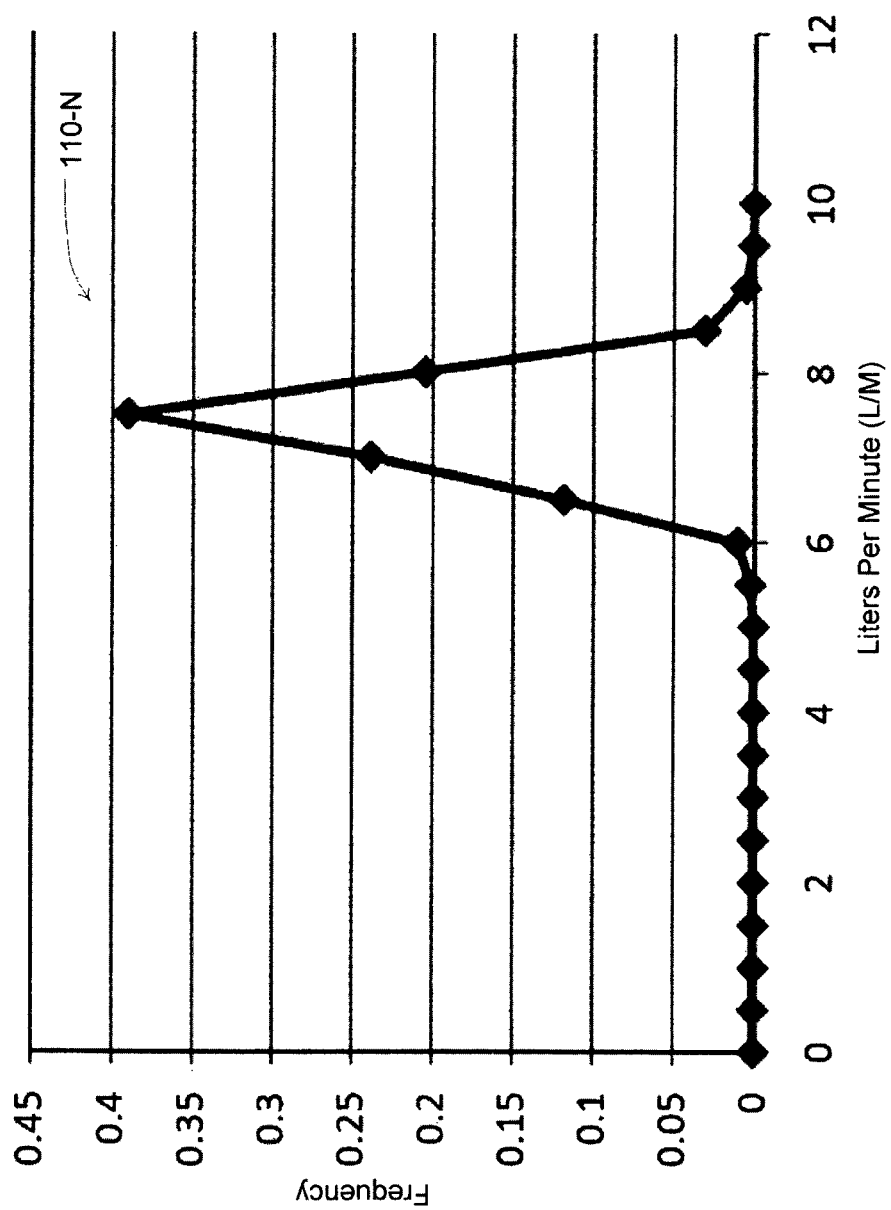
FIG. 4 is another example plot of a ventilation histogram based on the measures of FIG. 3 showing adequate ventilation.

An example ventilation assessment of the present technology may be considered in reference to FIGS. 3 and 4. FIG. 3 is a plot of respiratory data from a well-treated patient on CPAP during the course of a single night's treatment session. The included traces are (top-to-bottom), respiratory flow 330F, ventilation 330V, oxygen blood saturation ($SpO_2$) 330S and leak 330L. In this example, the ventilation signal, which is a low pass filtered absolute value of the respiratory flow signal with a time constant of 180 seconds, is stable over the whole night. The $SpO_2$ signal 330S is flat, not falling below about 94% at any time during the night. The leak signal 330L is also well controlled in that there are no substantial incidents of leak.

FIG. 4 shows a plotted ventilation histogram 110-N determined from the data of the ventilation signal 330V for the night. In the example, the ventilation values were assessed in bins or intervals of about 0.5 liters per minute. The frequency associated with each bin or interval may be determined as a percentage of the total treatment session (e.g., by the number of observed or sampled ventilation values in each interval divided by the total number of observed or sampled ventilation values during one treatment session). In some such embodiments, a determination that a single peak exists in the histogram and that the single peak is associated with an adequate ventilation value (e.g., 7.5 liters per minute) may be taken as an indicator of normal patient ventilation for the session. It will be understood that other measures of frequency and ventilation may be utilized for the ventilation histograms. For example, although the above ventilation histogram is illustrated showing a frequency distribution of minute ventilation values over the course of a single treatment session, some embodiments may also optionally permit generation of ventilation histograms using ventilation values from multiple treatment sessions (e.g., one week or one month of treatment sessions etc.).

In the aforementioned embodiment shown in FIG. 4, the example bin width of 0.5 liters/minute was chosen. However, bins can be set up in any way possible. There may be some standard strategies for histogram determination and bin selection that may be useful.

Such a histogram may be calculated by:
1. selecting an origin x0 (coinciding with point (0,0) in FIG. 4) and dividing the real line (e.g., the ventilation signal) into bins B of width h. Mathematically this may be represented as Bj=[x0+(j−1)h, x0+jh], j=1, 2, . . . .

2. Count how many observations fall into each bin Bj and denote the number of observations into bin j by $n_j$.
3. For each bin divide the frequency count by the sample size n (e.g., a treatment session) to convert them into relative frequency, and by the bin width $h \rightarrow f_j = n_j/nh$.

The bin width and origin point may have an important role in effectively characterizing the distribution of data. The origin point of the histogram may be chosen from anywhere along the Real line→an example choice might be Min (data)−range/10—where the range=Max(data)−Min(Data)]. Furthermore, another way to view the bin width parameter is to look at it as a smoothing parameter. If the bin width is too large, then the histogram will look flat, while if the bin width is too small, it will simply replicate the data. Thus, it can be important to choose an appropriate bin width.

There are a number of possible methods of choosing bin width:
1. The simplest approach is to inspect the data visually and select a bin width. An extension of this method is to find the max and min values of the data and divide that by the selected bin width.
2. Sturges formula: $h = \log 2(n) + 1 \Rightarrow$ where n=sample size
3. Scott's formula: $h = 3.5\sigma/n^{1/3}$ σ=sample standard deviation, n=sample size
4. Optimization techniques such as MISE and AMISE can be used to select the bin width.

In another example implementation, the histogram algorithm may include a method for dynamically determining bin width such that the bin width may be variable. In particular, variable bin width may be useful in characterizing sparsely distributed datasets. For example, if a patient has only limited time period where a hypoventilation episode was experienced, using a constant bin width may not present or detect this clearly. In such situations the use of a variable bin width can become very useful.

Kernel Density Estimate

Another implementation of the ventilation assessment methodology could be based on use of a kernel density estimator to capture the distribution of the ventilation signal. An advantage of this approach may be that it can effectively capture sharp features in the distribution, which in the case of characterizing the ventilation signal may become very useful. Furthermore, the selection of the origin point will not affect the characterization of the distribution.

Figure 5:
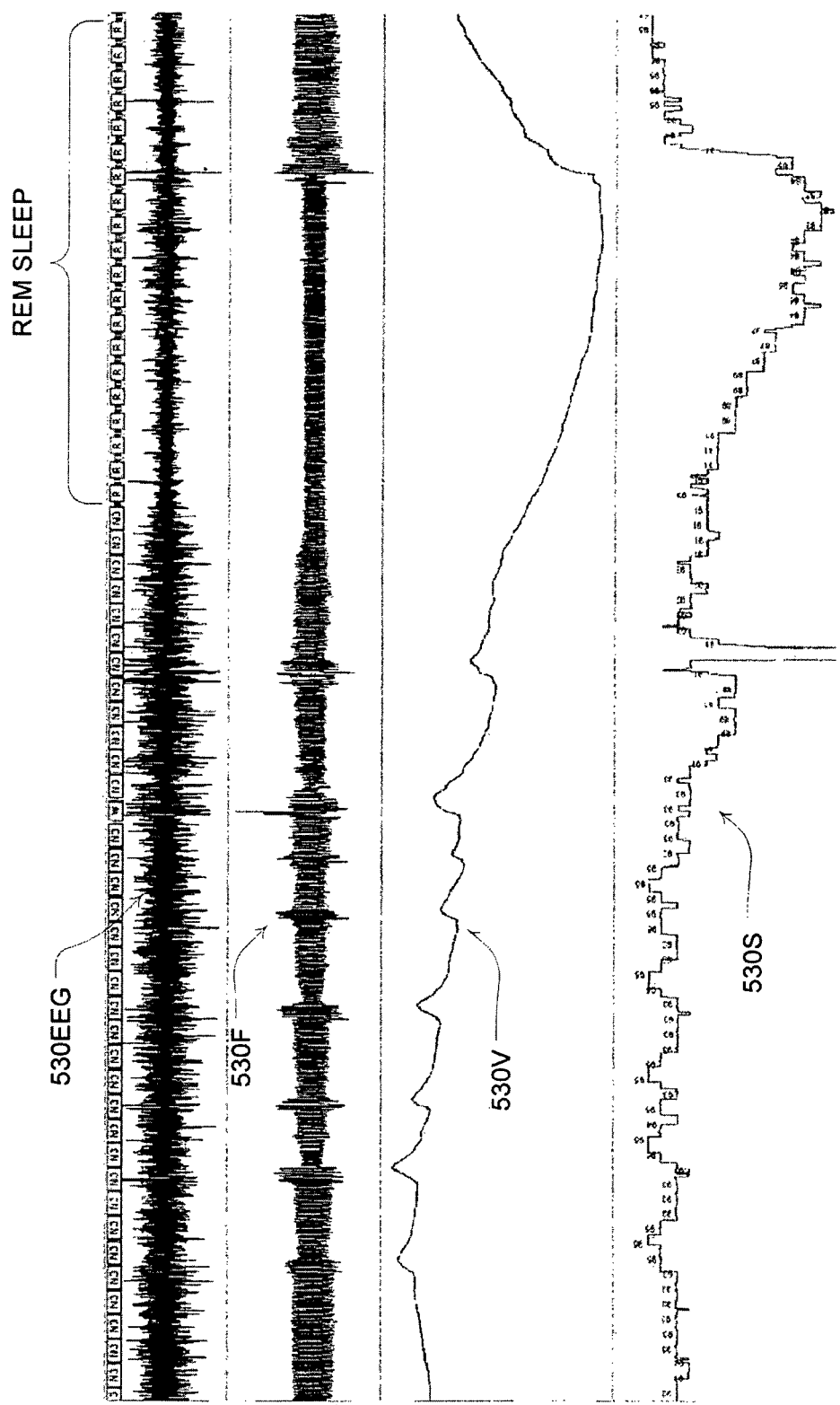
FIG. 5 is another graph showing a plot of flow, ventilation, oxygen saturation and electroencephalography signals during the course of a night's treatment session with a respiratory treatment apparatus.
Figure 6:
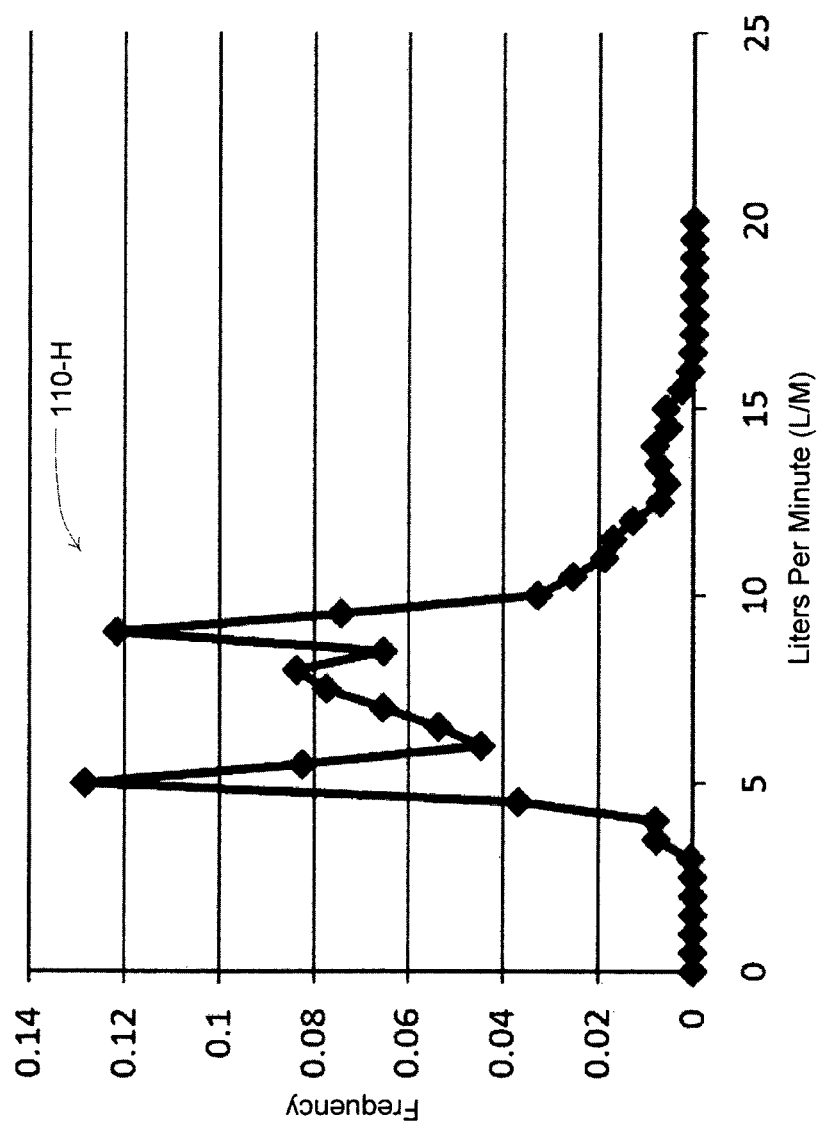
FIG. 6 is an example plot of a ventilation histogram based on the measures of FIG. 5 showing insufficient ventilation.
Figure 7:
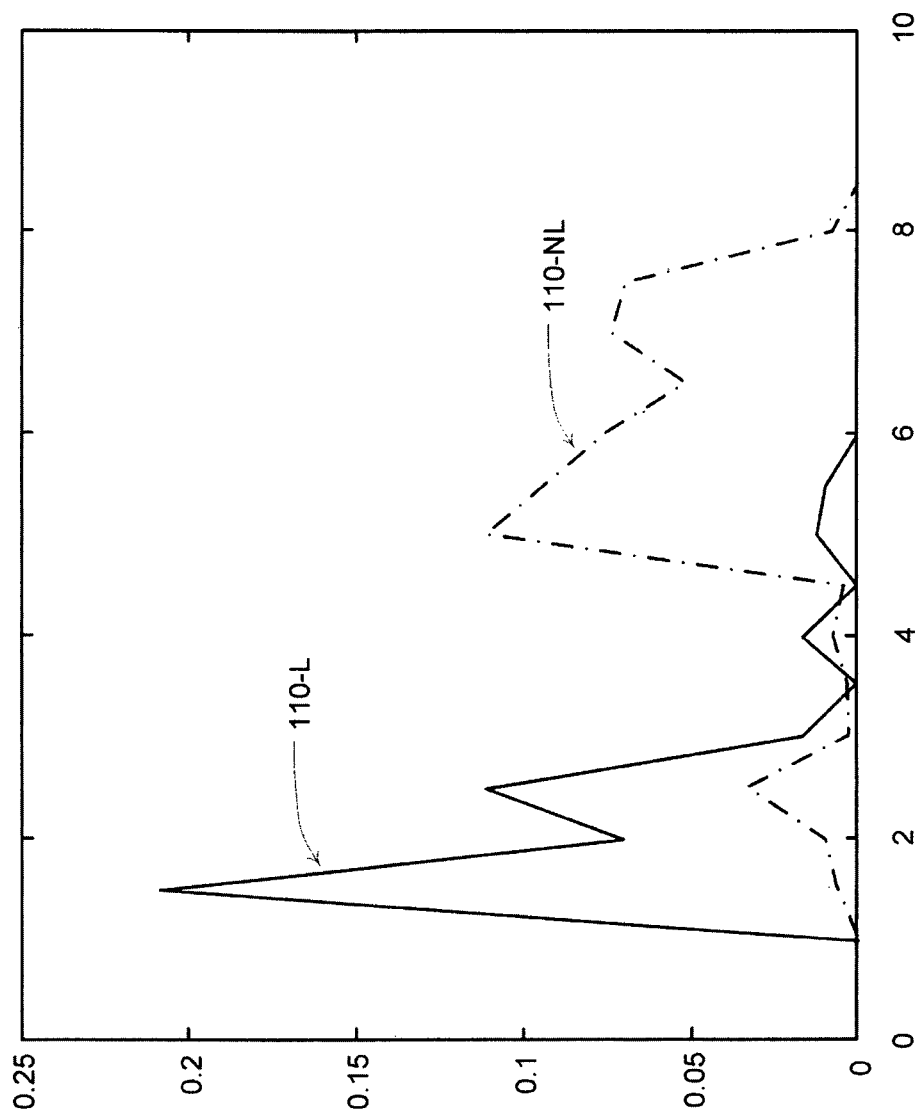
FIG. 7 is an example plot of leak partitioned ventilation histograms based on the measures of FIG. 5.

A further example ventilation assessment of the present technology may be considered in reference to FIGS. 5 and 6. FIG. 5 is a plot of respiratory data from a patient on CPAP experiencing hypoventilation during the course of a single night's treatment session. The included traces are (top-to-bottom), electroencephalography 530EEG, respiratory flow 530F, ventilation 530V and oxygen blood saturation (SpO$_2$) 530S. In this example, the ventilation signal, which is also a low pass filtered absolute value of the respiratory flow signal with a time constant of 180 seconds, falls for an extended period of time in the second half of the graph. The SpO$_2$ signal also falls for an extended period. FIG. 6 shows a plotted ventilation histogram 110-H determined from the data of the ventilation signal 530V for the night. By observation or analysis of the data of the ventilation histogram, conclusions about the state of the patient may be made. For example, analysis of the histogram may detect that the patient's ventilation has a bi-modal distribution. In some embodiments, this may be determined by detecting the existence of two peaks. If an evaluation of the ventilation value or interval attributable to either peak is indicative of low ventilation, the analysis may be taken as an indication of an incident of hypoventilation. In the example of FIG. 6, one peak is at approximately 5 liters per minute and the other peak is approximately 9 liters per minute. The peak at 5 liters per minute may be taken as an indicator of hypoventilation.

However, such analysis can be confounded by the existence of mouth leak. Thus, some embodiments of the ventilation assessment may partition ventilation data based on detection of leak. For example, a ventilation assessment device of the present technology may be combined with, or receive leak data from, a leak detector, such as a mouth leak detector. In some embodiments, the mouth leak detector may be implemented by one or more of the methodologies disclosed in U.S. Provisional Patent Application No. 61/369,247, filed on Jul. 30, 2010, the entire disclosure of which is incorporated herein by reference. Thus, based on a determination that leak is not present (e.g., a measure of leak is not greater than zero), a ventilation histogram may be evaluated. For example, a histogram may be based on ventilation values taken only from periods of treatment during which there is no leak. Thus, the histogram assessment may disregard ventilation values that are contemporaneous with periods of leak.

Optionally, another leak-related histogram may be computed based on ventilation values taken only from periods of treatment during which a mouth leak is detected. In such a case, the leak-related-histogram may then be evaluated to rule out a potential indication of hypoventilation that is based on the data of the more complete ventilation histogram that includes ventilation values from periods with and without leak.

Furthermore, awake periods, apneas, periodic breathing and arousals, which create relatively long term instability in ventilation during treatment, can also be confounding factors. Thus, some embodiments of the ventilation assessment may partition ventilation data based on detection of ventilatory instability. For example, a ventilation assessment device of the present technology may be combined with, or receive ventilatory stability data from, a ventilatory stability detector. In some embodiments, the ventilatory stability detector may be implemented by one or more of the methodologies, such as the methodology that derives a sleep stability measure, awake state, periodic breathing, arousals or other events or measures therein that may serve to imply stability, or lack thereof, for patient ventilation, as disclosed in U.S. Provisional Patent Application No. 61/226,069 filed Jul. 16, 2009 or International Patent Application No. PCT/AU2010/000894, filed Jul. 14, 2010, or U.S. patent application Ser. No. 13/383,341, filed on Jan. 10, 2012, the disclosures of which are incorporated herein by reference. Thus, based on a determination of ventilation stability (e.g., there is no Ventilatory Instability), a ventilation histogram may be evaluated. For example, a histogram may be based on ventilation values taken from periods of treatment during which the ventilatory stability detector suggests that the ventilation levels are stable and therefore will not corrupt the formation of the histogram.

In another embodiment, the ventilator stability index may be calculated as a rolling variance of another respiratory feature which is related to ventilation. An example of such a feature may be the inspiratory tidal volume. Others include expiratory tidal volume, whole breath tidal volume (e.g., an integration of the absolute value of a flow signal that is divided by breath length). The ventilation histogram may then be formed from ventilation values taken during treatment when the rolling variance of any of these features is below a predetermined threshold.

Furthermore, in another embodiment of the technology, calculation of the ventilation histogram may be performed in accordance with both a leak detector and a ventilation stability detector. In such a case, the resulting histogram would contain ventilation values during treatment periods characterized by ventilatory stability and an absence of leak.

(B) Example Respiratory Treatment Apparatus Embodiment

Figure 8:
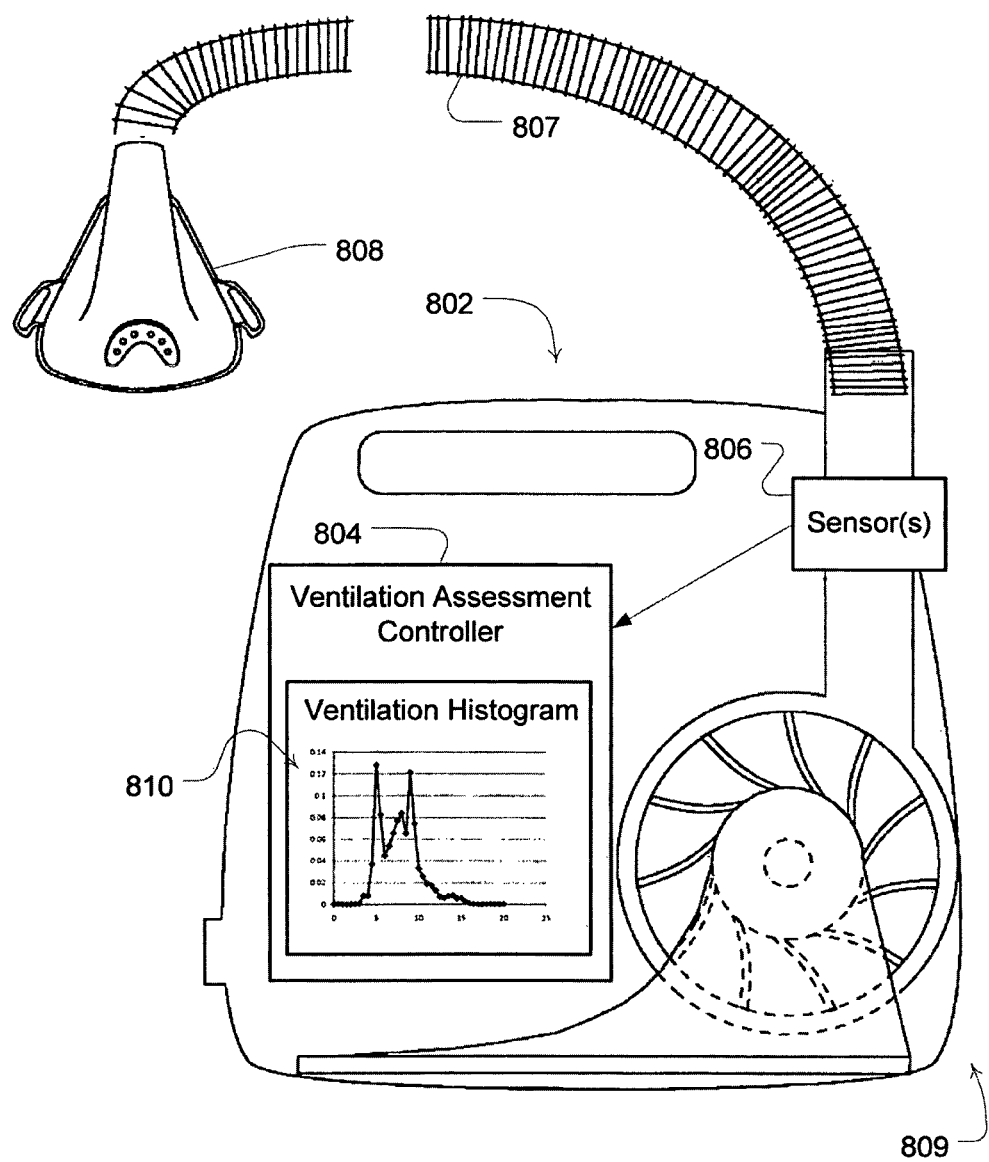
FIG. 8 is an illustration of an example pressure treatment apparatus with a ventilation assessment controller of the present technology.
Figure 9:
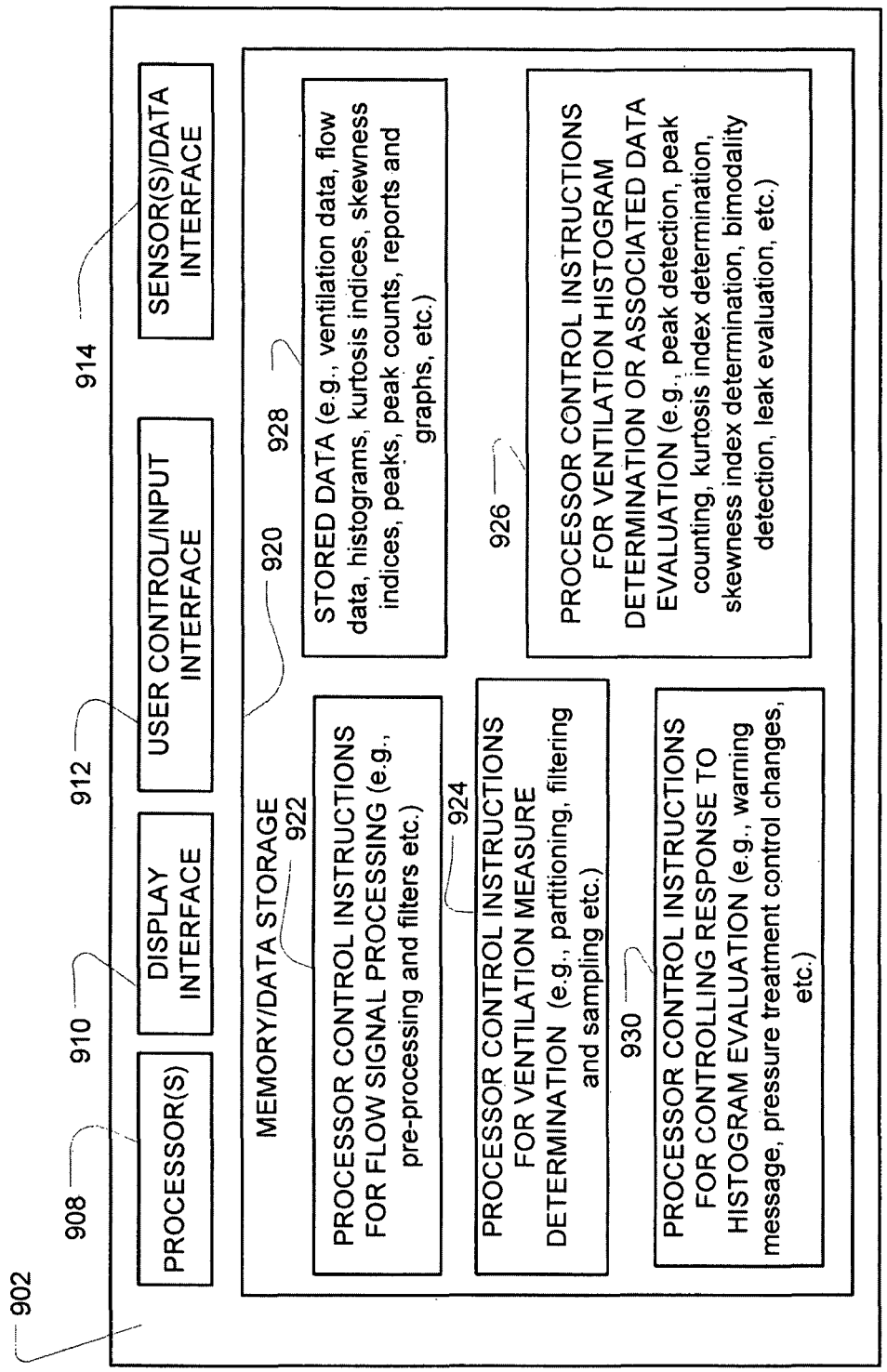
FIG. 9 is a block diagram of a controller for a ventilation detection apparatus including example components suitable for implementing the assessment methodologies of the present technology.
Figure 10:
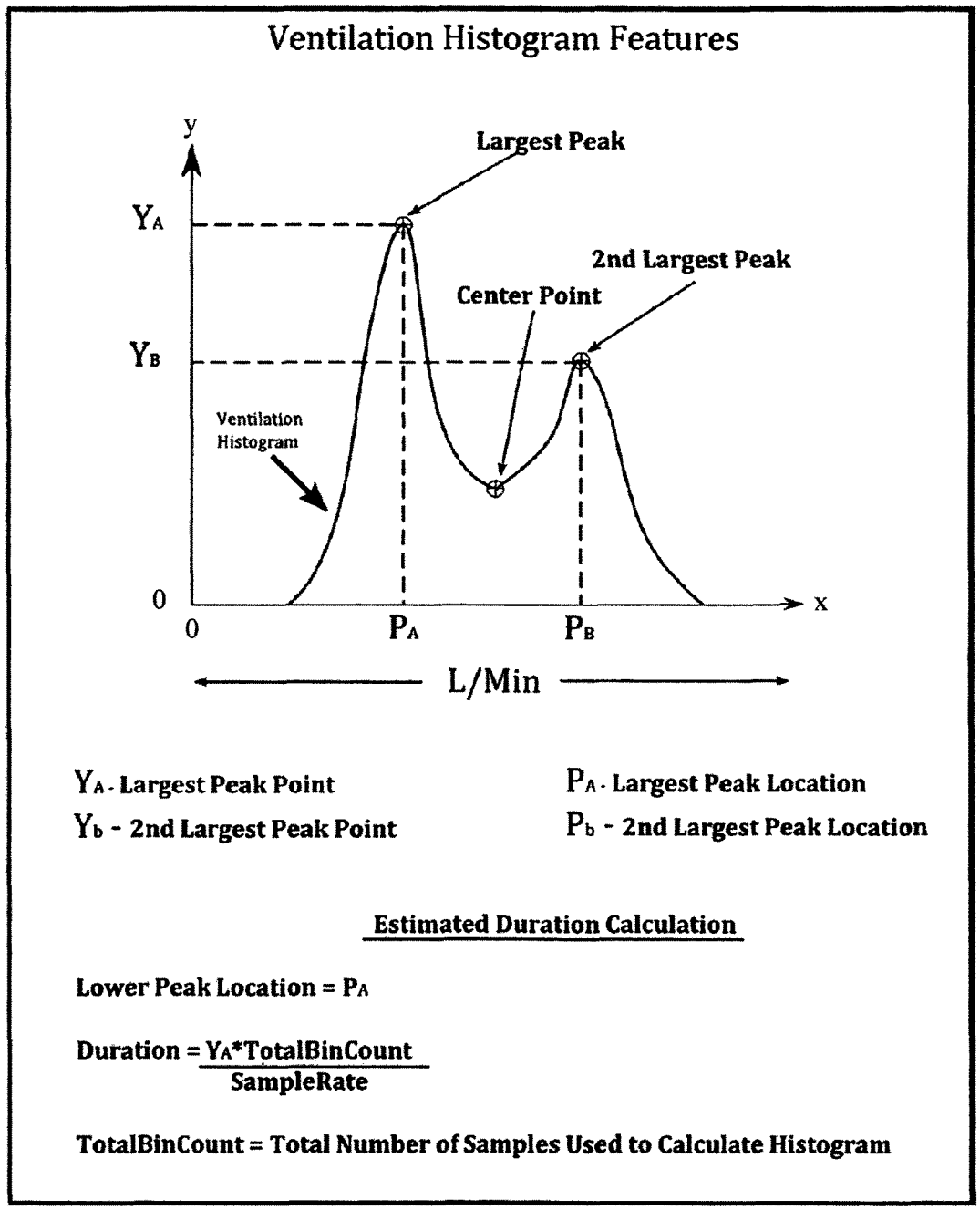
FIG. 10 is a graph of a ventilation histogram and illustrates a duration calculation based on the histogram.

In reference to FIG. 8, the present ventilation assessment technology may be implemented with a respiratory treatment apparatus 802, such as a CPAP device, or other respiratory treatment apparatus that provides pressurized breathable gas to a patient. (e.g., constant CPAP or bi-level CPAP). Such an apparatus may include a flow generator such as a servo-controlled blower 809. The blower 809 can typically include an air inlet and impeller driven by a motor (not shown).

The respiratory treatment apparatus 802 will also typically include, or be connectable to, a patient interface that may comprise an air delivery conduit 807 and a mask 808 to carry a flow of air or breathable gas to and/or from a patient. Optionally, as shown in FIG. 8, the mask may include a vent to provide an intentional leak.

The apparatus 802 also may include, or be connectable to, one or more sensors 806, such as a pressure sensor, flow sensor and/or an oximetry sensor. In such an embodiment, the pressure sensor, such as a pressure transducer, may measure the pressure generated by the blower 809 and generate a pressure signal p(t) indicative of the measurements of pressure. Similarly, the flow sensor generates a signal representative of the patient's respiratory flow. For example, flow proximate to the patient interface 808 or a sense tube (not shown) or flow proximate to the blower 809 may be measured using a pneumotachograph and differential pressure transducer or similar device such as one employing a bundle of tubes or ducts to derive a flow signal f(t). Optionally, if an integrated oximetry sensor is employed, the oximetry sensor may be a pulse oximeter to generate oximetry signals $O_2(t)$ indicative of blood gas saturation levels, such as oxygen saturation. Other sensors may be utilized to generate data indicative of flow, pressure or oximetry for the purposes of the methodologies of the apparatus 802.

Based on the sensor signals, such as the flow f(t) and/or pressure p(t) signals, a controller 804 may generate blower control signals. For example, the controller may generate a desired pressure set point and servo-control the speed of the blower to meet the set point by comparing the set point with the measured condition of the pressure sensor. Thus, the controller 804 may make controlled changes to the pressure delivered to the patient interface by the blower 809. Typically, such settings may be made to set a desired treatment pressure, to synchronize a treatment with patient respiration or to support the patient's respiration and may be made in conjunction with a detection of a state of a patient respiration such as by analysis of the flow signals in conjunction with control parameters such as trigger and cycling thresholds. Optionally, changes to pressure may be implemented by controlling an exhaust with a mechanical release valve (not shown) to increase or decrease the exhaust while maintaining a relatively constant blower speed. Similarly, based on flow f(t) and/or pressure p(t) signals, the controller 804 may implement the present ventilation assessment methodologies described in more detail herein.

Thus, the controller 804 may include one or more processors programmed to implement particular methodologies or algorithms described in more detail herein. To this end, the controller may include integrated chips, a memory and/or other control instruction, data or information storage medium. For example, programmed instructions encompassing such a control methodology may be coded on integrated chips in the memory of the device. Such instructions may also or alternatively be loaded as software or firmware using an appropriate data storage medium.

In some such embodiments, the controller may detect or score hypoventilation or hyperventilation events based on the evaluation of the ventilation histogram as discussed herein and modify pressure control parameters for the respiratory treatment based on the detection of such events. For example, if one or more of hypoventilation events have been detected, the controller may increase pressure or automatically change a treatment protocol to increase ventilation such as by switching to a bi-level PAP mode from a more constant CPAP mode. Similarly, if one or more of hyperventilation events have been detected, the controller may decrease pressure or automatically change a treatment protocol to decrease ventilation such as by switching from a bi-level CPAP mode to a more constant CPAP mode.

In some embodiments, the controller may generate warning or informational messages based on the ventilation assessment of the ventilation histogram. For example, the controller may display (e.g., on an LCD or other display device of the apparatus) and/or transmit (e.g., via wired or wireless communication or other data transfer) messages concerning the detection of hypoventilation or hyperventilation. The controller may also generate messages with the data of the ventilation histogram. The controller may also generate message to suggest further testing. For example, based on the evaluation of the ventilation histogram, such as a detection of hypoventilation, the controller may generate a message to suggest or request that the patient begin using a pulse oximeter sensor in a subsequent treatment session with the respiratory treatment apparatus. Thus, the controller may then initiate analysis of pulse oximetry data in a subsequent treatment session based on the analysis of the ventilation histogram from the prior session. The data of the pulse oximetry in a subsequent session may then be analyzed by the controller to confirm occurrence of ventilation inadequacy (e.g., hypoventilation) previously detected by analysis of the ventilation histogram. Further messages may then be generated by the device after analysis of the oximetry data to identify to the patient and/or physician that other treatment may be necessary due to over ventilation or under ventilation or may identify that ventilation is acceptable.

Other change's to the control parameters or messages from the respiratory treatment apparatus may also be made or suggested in accordance with the detection of the hypoventilation or hyperventilation based on the ventilation histogram evaluation.

(C) Further Example Ventilation Assessment Methodologies

In some embodiments of the ventilation assessment of the present technology, such as when the assessment is made by a controller of a respiratory treatment apparatus configured to provide a pressure treatment, any or all of the following steps or procedures may be implemented by the controller.

1. Measure flow ($Q_{FG}$) at a flow-generator (FG) of a pressure treatment apparatus;

2. Measure pressure ($P_{FG}$) at or near the flow-generator;

3. Using a known circuit impedance ($R_{cct}$), calculate a patient interface or mask pressure as $$P_{mask} = P_{FG} - Q_{FG} \times R_{cct}$$

4. Calculate the intentional leak (e.g., in the event of vent flow due to use of a mask with a vent) as a known function (f) of the pressure at the mask:

$$Q_{vent} = f(P_{mask})$$

5. Calculate the "mask flow" ($Q_{mask}$) as:

$$Q_{mask} = Q_{FG} - Q_{vent}$$

6. Calculate the instantaneous inadvertent or unintentional leak ($Q_{leak}$) (e.g., mouth leak by a method previously described and/or any leak detection method described in U.S. Pat. No. 6,659,101, the disclosure of which is incorporated herein by reference) as a function (f) of mask pressure and mask flow as:

$$Q_{leak} = f(P_{mask}, Q_{mask})$$

7. Calculate a patient respiratory flow estimate as:

$$Q_{resp} = Q_{mask} - Q_{leak}$$

8. Calculate the patient ventilation estimate as:

$$V = LP(0.5 \times |Qresp|)$$

where LP is, for example, a single pole low pass filter with a time constant of about 180 seconds;

9. Calculate a histogram of the patient ventilation estimate over the duration of the night or session;

10. Determine, using a peak detector or otherwise, if there is a peak in the histogram which is at, or very close to, zero ventilation. Remove this peak or raw data relating to this peak, if it is present. (Such data may be indicative of a prolonged period of missing or anomalous data capture such as if the flow generator is ON but no patient connected).

11. Calculate statistics from the histogram or the associated data. For example, determine an index representing the kurtosis (peakedness) and/or an index representing the skewness.

12. Evaluate distributions with excessive positive or negative skewness as a sign of hypoventilation or hypoventilation/hyperventilation. For example, if a skewness index exceeds a positive threshold, the comparison may be taken as, or a basis for, an indication of an occurrence of hypoventilation. Similarly, if the skewness index falls below a negative threshold, the comparison may be taken as, or as a basis for, an indication of an occurrence of hyperventilation. Suitable thresholds for these comparisons may be empirically determined.

13. Evaluate platykurtic distributions (e.g., kurtosis<1). This will typically indicate a flatter central portion (e.g., less "peakedness"). The threshold here may be set to 1. For example, a smaller Kurtosis value may be taken to mean that the histogram will have a smaller peak(s) and larger tails. This may typically be seen in a ventilation histogram of a patient with hypoventilation. In general, a standard normal distribution will have a kurtosis of 3 and a bi-modal distribution will have larger tails and a flatter peak in most cases.

14. Evaluate the distribution and determine if it is bimodal, for example, by detecting one or more peaks (e.g., a local maxima). If it is bimodal (e.g., two peaks are detected), check that the lower ventilation value attributable to one peak is indicative of a hypoventilation state by comparison of the ventilation value with a suitable threshold. Similarly, check that the other peak is attributable to a ventilation value that is indicative of normal breathing by comparison of the ventilation value with a suitable threshold. For example, ventilation values of between 6.5 and 8.5, more specifically between 7 and 8, such as 7.5 l/min., may serve as such thresholds indicative of normal ventilation.

15. Optionally, the distribution may be evaluated to determine bimodality by using an M-shape detection algorithm. This can serve as a metric for detecting the presence of bimodality. One such method is described in International Patent Application No. PCT/AU2008/000647, filed on May 9, 2008, the entire disclosure of which is incorporated herein by reference.

16. Check that the confirmation of hypoventilation is not caused or affected by excessive mouth leak (e.g., by analysis of the leak partitioned ventilation histogram(s) as mentioned above).

17. Report a metric, such as an Apnea Hypopnea Index) or calculated probability that the session of night flow data is indicative of someone experiencing hypoventilation.

18. Where a positive indication of hypoventilation is given, suggest a night or several nights with $SpO_2$ monitoring.

19. Confirm that hypoventilation is present from an $SpO_2$ recording using the typical "rules" for sleep-related hypoventilation/hypoxaemia.

Further Example Ventilation Assessment Procedures and Methodologies

Figure 11:
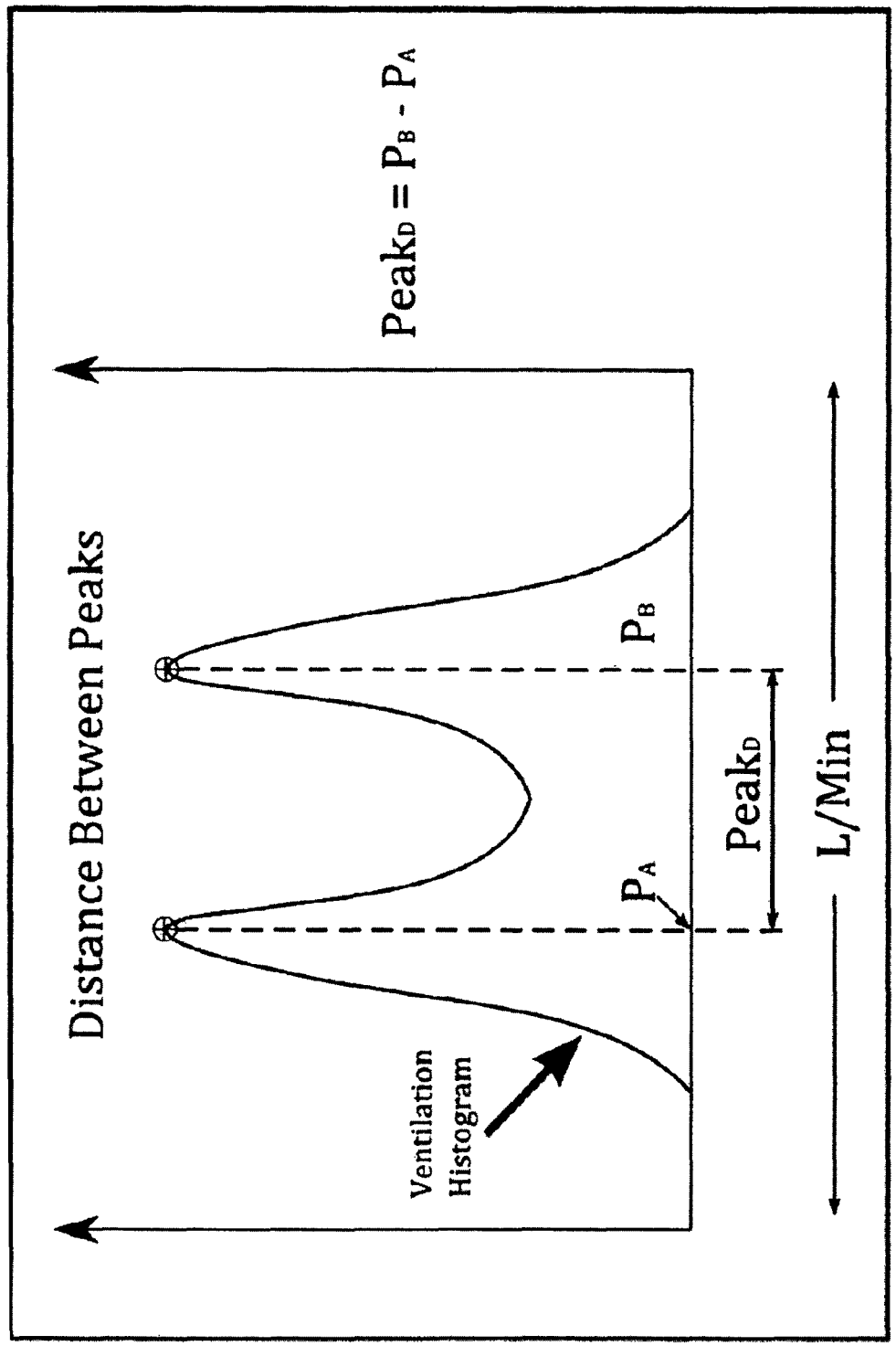
FIG. 11 is another graph of a ventilation histogram and illustrates a distance calculation based on peaks of the histogram.

One or more of the following steps or procedures may also be implemented in addition, or instead of, the ones described above. These steps or procedures, which may be controlled operations of one or more processors or controllers, may be considered with the illustrated graphs of FIGS. 10 through 17:

a. Calculate a histogram of the patient ventilation estimate over the duration of the night or session, such as one when there is little or NO leak and ventilatory stability exists.

b. Calculate the number of peaks of the histogram and their heights, such as the example heights $Y_A$ and $Y_B$ illustrated in FIG. 10, using a peak detector.

c. Calculate the distance between the two largest peaks in the histogram, such as the distance, $Peak_D$, between peak position $P_A$ and peak position $P_B$ as illustrated in FIG. 11;

d. Convert the distance between the two largest peaks into a probability space (such as a 0 to 1 probability space) using a transformation function. Generally, in the case of hypoventilation the further apart the two peaks are, the greater the chance that some sort of hypoventilation is occurring. In other words, one can expect a peak at the patient's 'natural' ventilation level and another peak at the patient's 'lower' ventilation level (which one expects to see during periods of hypoventilation). An example of a transformation function is provided in Table T below. However, any other function which can transform numbers associated with the distance between the peaks, from real number space into a probability space such as a 0 to 1 space, can be used.

TABLE T

| X (L/min) | G(X) (probability of occurrence of hypoventilation) |
| --- | --- |
| x < 0.15 | 0.0 |
| 0.05 ≤ x < 0.15 | 0.1 |
| 0.15 ≤ x < 0.2 | 0.13 |
| 0.2 ≤ x < 0.25 | 0.16 |
| 0.25 ≤ x < 0.3 | 0.2 |
| 0.35 ≤ x < 0.4 | 0.24 |
| 0.4 ≤ x < 0.45 | 0.28 |
| 0.45 ≤ x < 0.5 | 0.32 |
| 0.5 ≤ x < 0.55 | 0.38 |
| 0.55 ≤ x < 0.6 | 0.45 |
| 0.6 ≤ x < 0.65 | 0.52 |

TABLE T-continued

| X (L/min) | G(X) (probability of occurrence of hypoventilation) |
|---|---|
| 0.65 ≤ x < 0.7 | 0.6 |
| 0.7 ≤ x < 0.75 | 0.68 |
| 0.75 ≤ x < 0.8 | 0.76 |
| 0.8 ≤ x < 0.85 | 0.8 |
| 0.85 ≤ x | 0.85 |

Using the patient ventilation histogram one can also estimate a duration of hypoventilation. The X coordinate of the lower of the peaks (e.g., $P_A$), indicates the ventilation level at which the lower peak is occurring and can be taken as the level of hypoventilation. The amplitude of the peak (e.g., $Y_A$) indicates the number of 3-minute periods during which the particular ventilation has been detected and, thus, can be used to estimate the overall duration during which the given ventilation has been measured. A processor may be configured to calculate the estimated duration with the example formula illustrated in FIG. 10.

Figure 16:
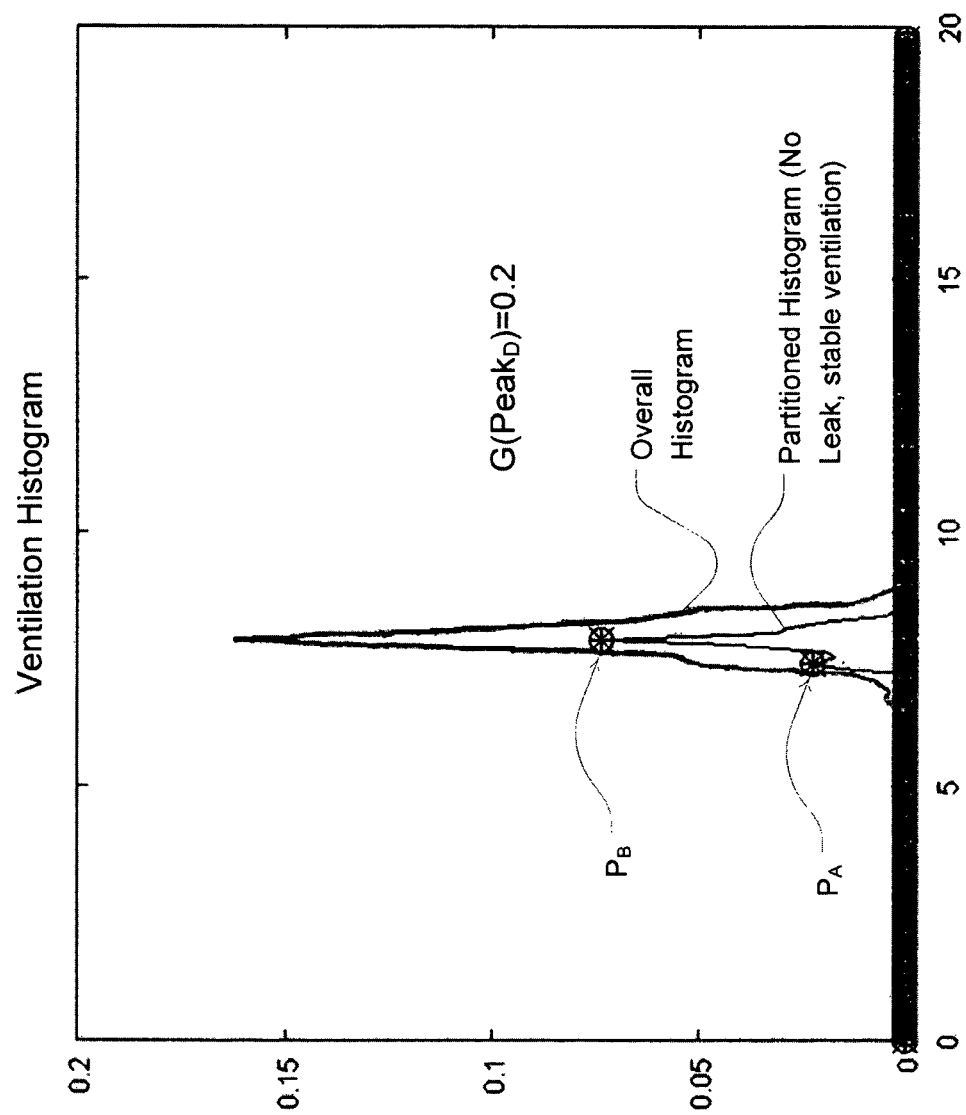
FIGS. 16 and 17 show examples of overall ventilation histograms and partitioned ventilation histograms with hypoventilation indicators.
Figure 17:
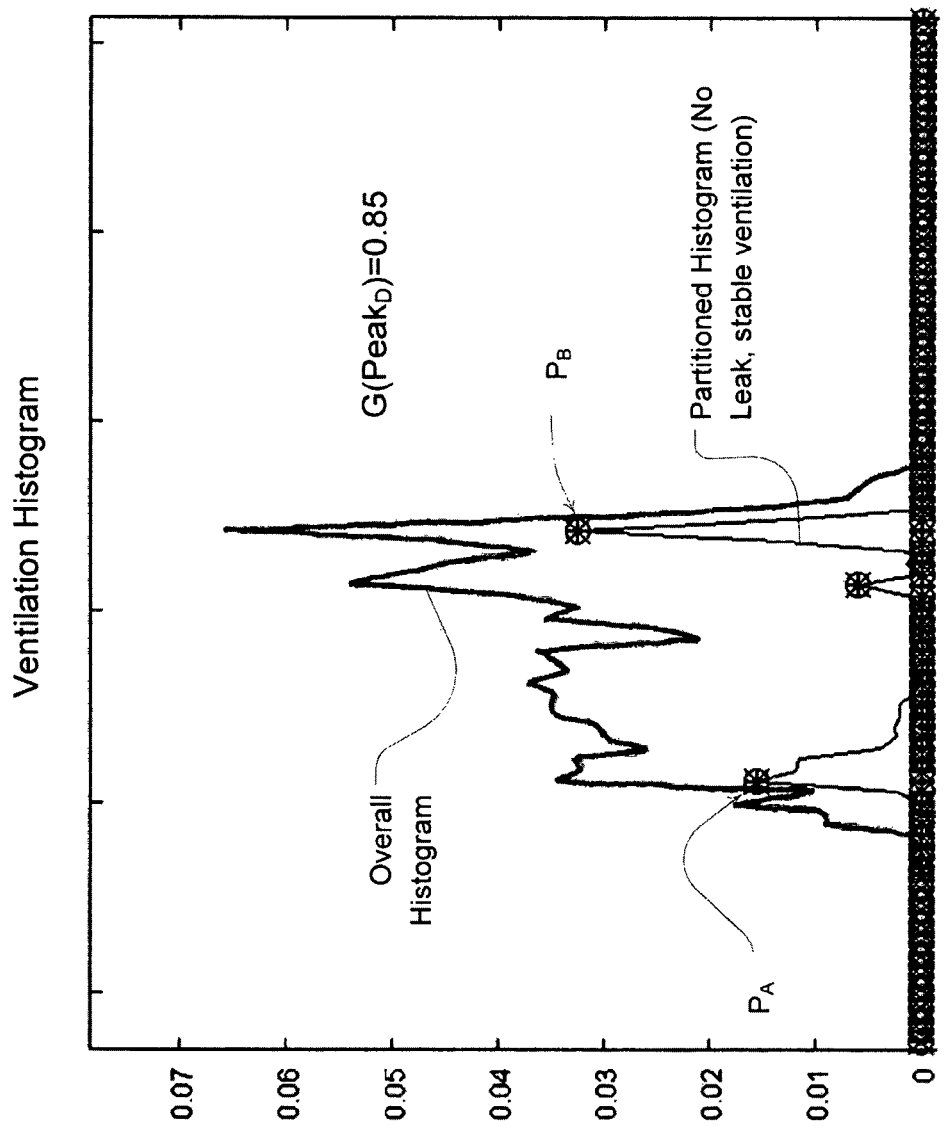

A metric or probability may be reported (e.g., recorded or generated as output) to provide an indication of the likelihood that the session of night flow data is indicative of someone experiencing hypoventilation. FIG. 16 shows an example of a substantially single-peaked histogram for which the probability classification system based on function G(x) of Table T returns a 'low' probability of 0.2. Such a low probability may be taken as an indication that presence of hypoventilation is unlikely. FIG. 17, on the other hand, shows an example of a bimodal histogram for which the probability classification system has returned a 'high' probability of 0.85. This may be taken as an indication that the presence of hypoventilation is highly likely. In some embodiments, the processor may generate the metric and/or the histogram graph to provide the indication of hypoventilation, such as the hypoventilation probability value, the hypoventilation value and/or the level of hypoventilation in association with the hypoventilation probability value.

The reported results may then be implemented for providing an indication of further treatment. For example, a positive indication of hypoventilation may be taken as a suggestion for a night or several nights $SpO_2$ monitoring. In one such embodiment, a processor may evaluate the reported probability by a comparison of the probability with one or more thresholds. Based on the comparison(s), a message may be generated to suggest additional testing (e.g., further $SpO_2$ monitoring) or some other treatment. Optionally, such a comparison may serve as a trigger to control further testing or treatment, such as a change in control of a generated pressure treatment with a respiratory treatment apparatus (e.g., an increase in pressure support (PS) ventilation or, an initiation of pressure support ventilation so as to servo control a measure of ventilation to satisfy a target ventilation) or a further evaluation.

For example, in some such cases, the apparatus 102 may also be configured to evaluate blood gas, such as with an oximeter that may be controlled with a processor of the apparatus. The processor may, based on the evaluation of the histogram, confirm that hypoventilation is present by controlling an analysis of $SpO_2$ data. In such a case, the processor may be configured to implement typical "rules" for sleep-related hypoventilation/hypoxaemia detection from blood gas. The processor may then generate, as output, the determinations based on each or both of the ventilation histogram evaluation and the blood gas evaluation.

Figure 12:
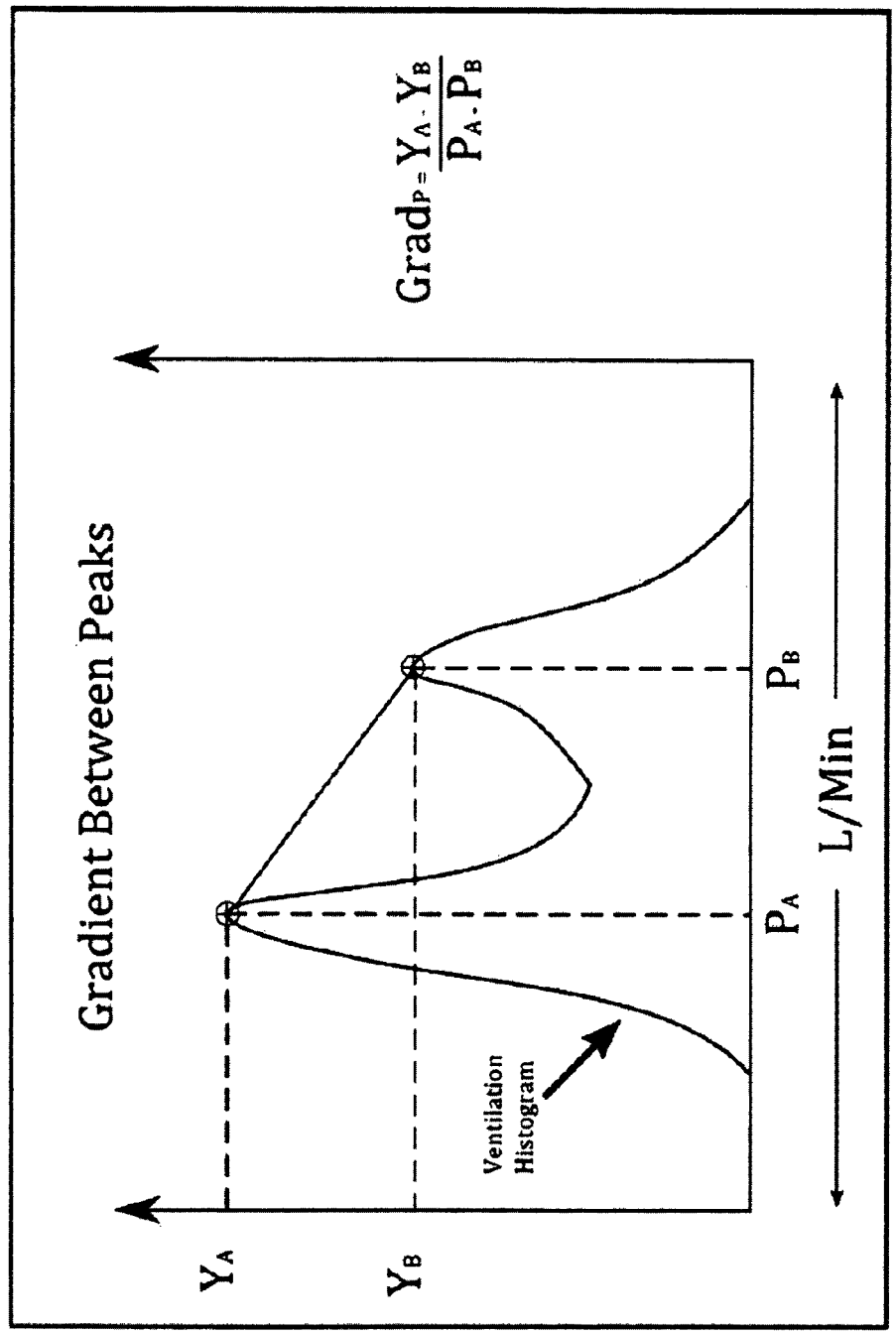
FIG. 12 is another graph of a ventilation histogram and illustrates a gradient calculation based on peaks of the histogram.
Figure 13:
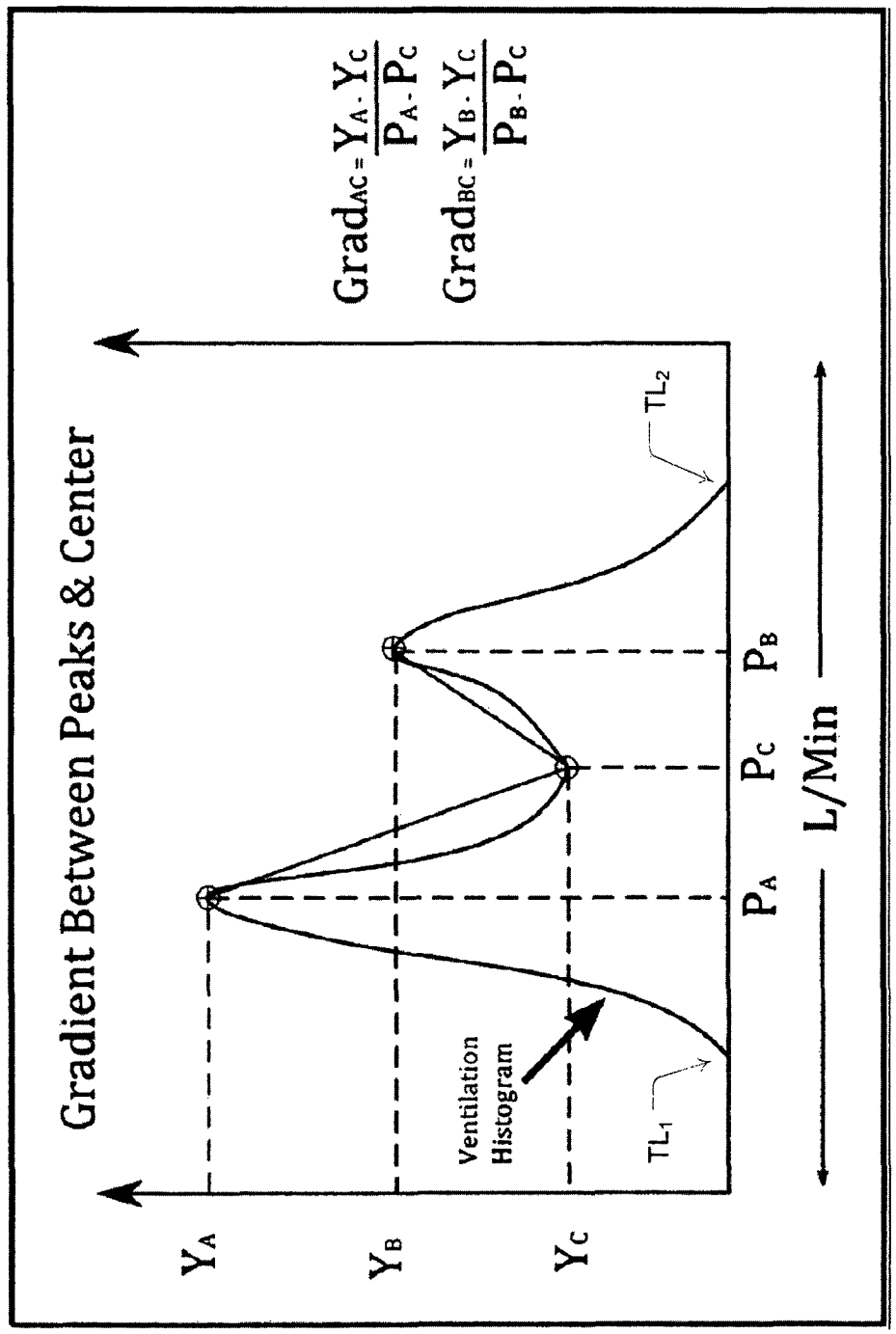
FIG. 13 is another graph of a ventilation histogram and illustrates additional gradient calculations based on peaks and a center point of the histogram.
Figure 14:
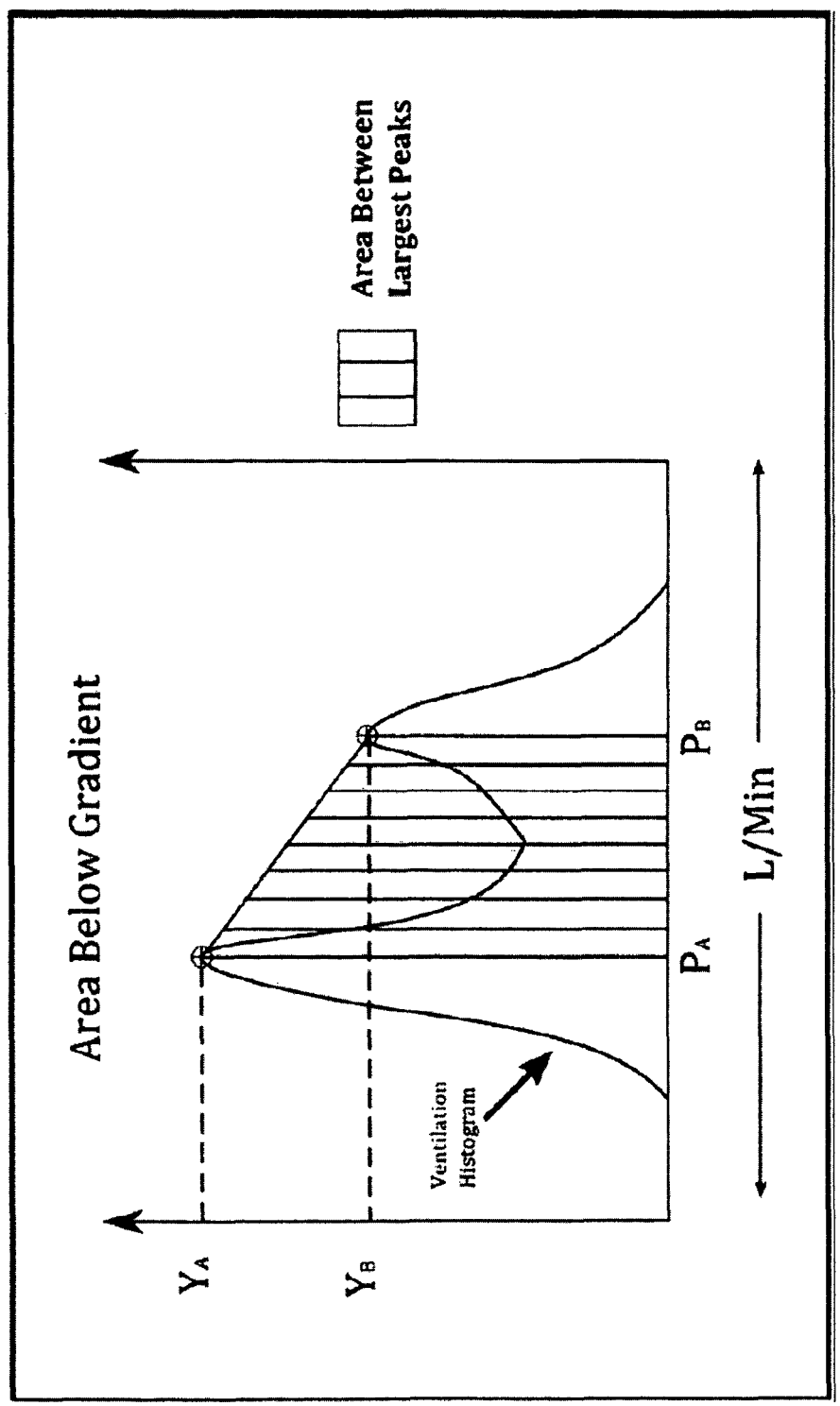
FIGS. 14 and 15 show additional ventilation histograms and illustrate several area calculations based on gradients defined by peaks and a center point of the histogram.
Figure 15:
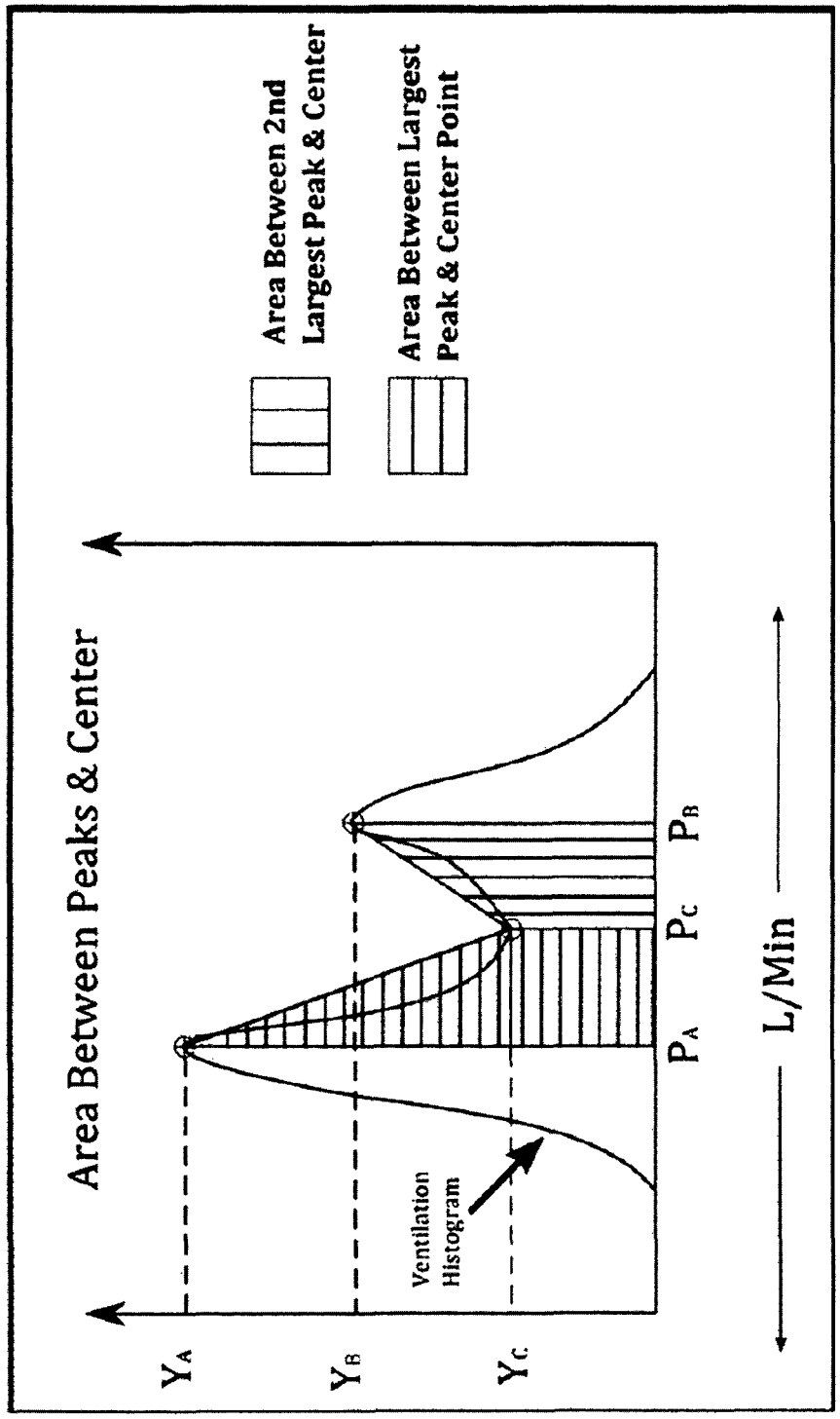

In a further implementation one or more of the following procedures or steps may also be implemented by one or more processors:

a. Calculate the peaks of the calculated patient ventilation histogram (either an overall histogram or an instability-free histogram) such as with a peak detector;

b. Calculate a midpoint, such as the center of the histogram, which may be the midpoint $P_C$ between the two extreme points (TL1 and TL2) of the tails of the histogram, as (shown in FIG. 13);

c. Calculate the distance $Peak_D$ between the two largest peaks in the histogram as previously described with reference to FIG. 11;

d. Calculate one or more gradients, such as the gradient of the line connecting the two largest peaks in the histogram. An example formula for the calculation of such a gradient is illustrated in FIG. 12;

e. Calculate the gradient between the largest peak & center point (e.g., gradient $Grad_{AC}$) such as with the formula illustrated in the example of FIG. 13.

f. Calculate the gradient between the $2^{nd}$ largest peak & center point (e.g., gradient $Grad_{BC}$) such as with the formula illustrated in the example of FIG. 13;

g. Calculate the area between the peaks as a function of one or more of the gradients, such as the area marked by vertical lines in FIG. 14, the area between the largest peak and center point as illustrated with the horizontal lines of FIG. 15; and/or the area between the second largest peak and center point as illustrated with the vertical lines of FIG. 15;

h. Calculate one or more shape features such as a shape feature using an M-shape detector or detection algorithm. This can serve as a metric for detecting the presence of bimodality. One such method is described in International Patent Application No. PCT/AU2008/000647, filed on May 9, 2008, the entire disclosure of which is incorporated herein by reference. Optionally, other or additional shape features based on other shape detection functions may be implemented.

i. Convert the gradient between the two largest peaks into a probability space, such as a 0 to 1 space, with a transformation function. If the gradient is either highly positive or highly negative, it may serve as an indication that the peak locations are too close or the smaller peak is too small. This may be seen in a histogram of a patient without hypoventilation and so the probability of hypoventilation associated with highly positive or highly negative gradient can be close to 0 according to the transformation function. The probability will get closer to 1 as the gradients get closer to 0 according to such a function.

j. Convert the gradient between the largest peak & center point into a probability space, such as a 0 to 1 probability space, using a transformation function. If the gradient is either highly positive or highly negative, it may serve as an indication that the peak locations are too close or the smaller peak is too small. This may be seen in a histogram of a patient without hypoventilation and in such a case, the probability of hypoventilation can be close to 0 according to the transformation function. The probability will get closer to 1 as the gradients get closer to 0 according to such a function.

k. Convert the gradient between the $2^{nd}$ largest peak & center point into a probability space, such as the 0 to 1 probability space, using a transformation function. If the gradient, is either highly positive or highly negative, it may serve as an indication that the peak locations are too close or the smaller peak is too small. This may be seen in a histogram of a patient without hypoventilation and so the hypoventilation probability can be close to 0 according to the transformation function. The probability can get closer to 1 as the gradients get closer to 0 with such a function.

l. Convert the area between the peaks into a probability space, such as a probability space between 0 and 1, using a transformation function. If the area is sufficiently large, then it would be indicative of the peaks being sufficiently far apart. The hypoventilation probability in such cases can approach 1 according to the probability function. For smaller areas as they decrease, the probability can approach 0 with such a function.

m. Convert the area between the largest peak and the center point into a probability space, such as a 0 to 1 probability space, using a transformation function. If the area is sufficiently large, then it may serve as an indication of the peaks being sufficiently far apart. For such increasingly large area cases, the probability can approach 1 according to such a probability function. For smaller areas as they decrease, the probability can approach 0 with such a function.

n. Convert a shape feature into a probability space, such as a probability space between 0 and 1, using a transformation function. Such an implemented transformation function will depend on the nature of the approximation function used to calculate the shape feature.

o. Calculate the kurtosis and skewness of the distribution characterized by the histogram.

p. Transform the kurtosis and skewness into a probability space, such as a 0 to 1 probability space, using a transformation function. A positive skewness may be taken as an indication of, a higher chance of hypoventilation occurring and so the transformation probability can be closer to 1 for positive values. Negative skewness values may indicate a lower chance of hypoventilation occurring and so the hypoventilation probability maybe closer to 0 according to such a function. A higher kurtosis may be taken as an indication of a higher chance of hypoventilation occurring and so the transformation probability can be closer to 1 according to such a function. Lower kurtosis values can be taken as an indication of a lower chance of hypoventilation occurring and so the hypoventilation probability may approach 0 according so such a function.

With such procedures, one or more features of a set of features can be generated. Such features may include:

a. Transformed gradient between the two largest peaks;
b. Transformed gradient between the largest peak and the center point;
c. Transformed gradient between the second largest peak and the center point;
d. Transformed area between two largest peaks;
e. Transformed area between the largest peak and the center point;
f. Transformed area between the second largest peak and the center point;
g. Transformed shape feature;
h. Transformed kurtosis feature;
i. Transformed skewness feature;

The transformation functions associated with each of these features as previously described may be determined either empirically or created on the basis of externally published data.

In some embodiments, based on the set of features, a processor may be implemented to calculate a hypoventilation probability, such as with a classification algorithm. Some or all of the above features may be evaluated. Weighting coefficients may also be implemented. In some such cases, the set of transformation probabilities or weighted probabilities may be compared to set of thresholds to assess the overall likelihood of hypoventilation given the values of the transformation probabilities. In one particular embodiment, a linear classifier could be implemented by a processor to calculate the overall hypoventilation probability. However other classification methods which can utilize the above mentioned features such as Bayesian Classification can be employed to calculate a final hypoventilation probability. As with previous embodiments, the hypoventilation probability may be reported as output. An evaluation of the value may be performed, such as by comparison with one or more thresholds, to control a further treatment or evaluation or generation of a message as previously described.

(D) Example System Architecture

An example, system architecture of a controller of the device of FIG. 1 or FIG. 8 is illustrated in the block diagram of FIG. 8. In the illustration, the ventilation assessment device 902 or general purpose computer may include one or more processors 908. The device may also include a display interface 910 to output ventilation detection reports (e.g., ventilation histogram data, hypoventilation event data, hyperventilation event data, skewness indices, kurtosis, indices, and/or ventilation values etc.), results or graphs (e.g., plotted ventilation histograms and/or signal traces as illustrated in the examples of FIGS. 3, 4, 5, 6 and 7) as described herein such as on a monitor or LCD panel. A user control/input interface 912, for example, for a keyboard, touch panel, control buttons, mouse etc. may also be provided to activate the methodologies described herein. The device may also include a sensor or data interface 914, such as a bus, for receiving/transmitting data such as programming instructions, oximetery data, flow data, pressure data, ventilation value data, ventilation histogram data etc. The device may also typically include a memory/data storage components containing control instructions of the aforementioned methodologies (e.g., FIG. 2). These may include processor control instructions for flow signal processing (e.g., pre-processing methods, filters) at 922 as discussed in more detail herein. They may also include processor control instructions for ventilation measure determination (e.g., partitioning, filtering and sampling etc.) at 924. They may also include processor control instructions for ventilation histogram determination or associated data evaluation (e.g., peak detection, peak counting, feature analysis, transformation functions, kurtosis index determination and thresholding, skewness index determination and thresholding, bimodality detection, leak evaluation, hypoventilation and/or hyperventilation scoring etc.) at 926. They may also include stored data 928 for these methodologies such as ventilation data, flow data, histograms, kurtosis indices, skewness indices, peaks, peak counts, gradients, transformation probabilities, reports and graphs, etc. Finally, they may also include processor control instructions for controlling responses to histogram evaluation (s) at 930 such as warning or information message generation, pressure treatment control changes, further testing control, etc.

In some embodiments, the processor control instructions and data for controlling the above described methodologies may be contained in a computer readable recording medium as software for use by a general purpose computer so that the general purpose computer may serve as a specific purpose computer according to any of the methodologies discussed herein upon loading the software into the general purpose computer. For example, the special purpose computer may not need to be configured to control pressure treatment or measure pressure or flow data. Rather, the computer may merely access such data, that may optionally be transferred from a respiratory treatment apparatus. The computer may then perform the ventilation assessment methodologies described herein such as the histogram determination and analysis based on the transferred data and may generate warning or informational messages based thereon.

In the foregoing description and in the accompanying drawings, specific terminology, equations and drawing symbols are set forth to provide a thorough understanding of the present technology. In some instances, the terminology and symbols may imply specific details that are not required to practice the technology. For example, although process steps in the assessment methodologies have been described or illustrated in the figures in an order, such an ordering is not required. Those skilled in the art will recognize that such ordering may be modified and/or aspects thereof may be conducted in parallel.

Moreover, although the technology herein has been described with reference to particular embodiments, it is to be understood that these embodiments are merely illustrative of the principles and applications of the technology. It is therefore to be understood that numerous modifications may be made to the illustrative embodiments and that other arrangements, may be devised without departing from the spirit and scope of the technology.

The invention claimed is:

1. A method for controlling a processor to assess sufficiency of ventilation from a measured flow of breathable gas, the method comprising:
   measuring, by way of a sensor, a flow of breathable gas representative of patient respiration;
   deriving measures of ventilation from the measure of flow;
   determining, with a processor, a histogram including the measures of ventilation, wherein the measures are volumes of breathable gas measured over a time interval; and
   evaluating the histogram in the processor and, based on the evaluation, outputting an indication of occurrence of hypoventilation.

2. The method of claim 1 further comprising displaying a graph of the histogram on a visual display device.

3. The method of claim 1 wherein the histogram represents a frequency distribution of ventilation values taken over the course of a treatment session, each ventilation value comprising a measure of volume over a time interval, the time interval being shorter than the time of the treatment session.

4. The method of claim 3 wherein the time interval is on an order of a minute and the time of the treatment session is on an order of hours.

5. The method of claim 1 further comprising:
   processing, in the processor, data associated with the histogram to calculate a skewness index;
   comparing the skewness index to a threshold; and
   indicating hypoventilation based on the comparison.

6. The method of claim 1 further comprising:
   processing, in the processor, data associated with the histogram to detect a number of peaks of the histogram; and
   indicating a presence or absence of hypoventilation based on the number of detected peaks.

7. The method of claim 1 further comprising:
   processing, in the processor, data associated with the histogram to determine a kurtosis index;
   comparing the kurtosis index to a threshold; and
   indicating a presence or absence of hypoventilation based on the comparison.

8. The method of claim 1 further comprising controlling, with the processor, measuring of the flow of breathable gas, wherein the sensor is a flow sensor.

9. The method of claim 1 further comprising processing data representing the histogram to generate a hypoventilation indicator, the indicator representing an occurrence of an event of hypoventilation.

10. The method of claim 9 wherein the hypoventilation indicator comprises a probability value.

11. The method of claim 9 wherein the processing comprises a detection of peaks of the histogram.

12. The method of claim 11 wherein the processing comprises calculating a distance between peaks of the histogram and transforming the distance into a probability space.

13. The method of claim 11 wherein the processing comprises calculating a gradient between peaks of the histogram.

14. The method of claim 13 wherein the processing comprises calculating an area with respect to the gradient and transforming the area into a probability space.

15. The method of claim 9 wherein the processing comprises calculating a set of features of the histogram and generating the indicator based on an evaluation of the set of features.

16. The method of claim 15 wherein the set of features comprises two or more of the following features: a gradient between two largest peaks, a gradient between a largest peak and a center point, a gradient between a second largest peak and a center point, an area between two largest peaks, an area between a largest peak and a center point, an area between a second largest peak and a center point, a shape feature, kurtosis value and skewness value.

17. The method of claim 1 further comprising determining a measure of leak and distinguishing measures of ventilation for the histogram based on the measure of leak.

18. The method of claim 1 further comprising determining a measure of ventilation stability and distinguishing measures of ventilation for the histogram based on the measure of stability.

19. The method of claim 18 wherein the determining the measure of ventilation stability comprises any of one or more of a detection of an awake period, an apnea event, a periodic breathing event and an arousal event.

20. The method of claim 1 further comprising processing data representing the histogram to generate a hyperventilation indicator, the indicator representing an occurrence of an event of hyperventilation.

21. The method of claim 1 wherein the method further comprises, based on the evaluating, changing an operational parameter of a respiratory treatment apparatus assisting the patient's respiration.

22. A method for controlling a processor to assess sufficiency of ventilation from a measured flow of breathable gas, the method comprising:
   measuring, by way of a sensor, a flow of breathable gas representative of patient respiration;
   deriving measures of ventilation from the measure of flow;
   determining, with a processor, a histogram including the measures of ventilation, wherein the measures are volumes of breathable gas measured over a time interval; and
   evaluating the histogram in the processor and, based on the evaluation, outputting an indication of occurrence of hyperventilation, wherein the method comprises:
processing, in the processor, data associated with the histogram to calculate a skewness index;
comparing the skewness index to a threshold, and
indicating hyperventilation based on the comparison.

23. A ventilation assessment apparatus comprising:
a flow sensor configured to measure a flow of breathable gas, and
a controller having at least one processor to access data representing a measured flow of breathable gas attributable to patient respiration obtained from the flow sensor, the controller being further configured to (a) control measuring of the flow of breathable gas with the flow sensor, (b) derive measures of ventilation from the measure of flow, (c) determine a histogram of the measures of ventilation, wherein the measures are volumes of breathable gas measured over a time interval and (d) evaluate the histogram in the processor and, based on the evaluation, output an indication of occurrence of hypoventilation.

24. The apparatus of claim 23 wherein the controller is further configured to display a graph of the histogram on a visual display device.

25. The apparatus of claim 23 wherein the histogram represents a frequency distribution of ventilation values taken over the course of a treatment session, each ventilation value comprising a measure of volume over a time interval, the time interval being shorter than the time of the treatment session.

26. The apparatus of claim 25 wherein the time interval is on an order of a minute and the time of the treatment session is on an order of hours.

27. The apparatus of claim 23 wherein the controller is further configured to:
process data associated with the histogram to calculate a skewness index;
compare the skewness index to a threshold; and
indicate an occurrence of hypoventilation based on the comparison.

28. The apparatus of claim 23 wherein the controller is further configured to:
process data associated with the histogram to detect a number of peaks of the histogram; and
indicate a presence or absence of hypoventilation based on the number of detected peaks.

29. The apparatus of claim 23 wherein the controller is further configured to:
process data associated with the histogram to determine a kurtosis index;
compare the kurtosis index to a threshold; and
indicate a presence or absence of hypoventilation based on the comparison.

30. The apparatus of claim 23 further comprising:
a flow generator configured to produce a breathable gas for a patient at a pressure above atmospheric pressure;
wherein the controller is further configured to control the flow generator to produce the breathable gas according to a pressure therapy regime based on an assessment of any one or more of (a) the histogram, (b) a number of peaks of the histogram, (c) a kurtosis index determined from data associated with the histogram and (d) a skewness index determined from data associated with the histogram.

31. The apparatus of claim 23 wherein the controller is configured to process data representing the histogram to generate a hypoventilation indicator, the indicator representing an occurrence of an event of hypoventilation.

32. The apparatus of claim 31 wherein the hypoventilation indicator comprises a probability value.

33. The apparatus of claim 31 wherein the controller is configured to detect peaks of the histogram.

34. The apparatus of claim 33 wherein the controller is configured to calculate a distance between peaks of the histogram and transforming the distance into a probability space.

35. The apparatus of claim 33 wherein the controller is configured to calculate a gradient between peaks of the histogram.

36. The apparatus of claim 35 wherein the controller is configured to calculate an area with respect to the gradient and transform the area into a probability space.

37. The apparatus of claim 31 wherein the controller is configured to calculate a set of features of the histogram and to generate the indicator based on an evaluation of the set of features.

38. The apparatus of claim 37 wherein the set of features comprises two or more of the following features: a gradient between two largest peaks, a gradient between a largest peak and a center point, a gradient between a second largest peak and a center point, an area between two largest peaks, an area between a largest peak and a center point, an area between a second largest peak and a center point, a shape feature, kurtosis value and skewness value.

39. The apparatus of claim 23 wherein the controller is configured to determine a measure of leak and to distinguish the measures of ventilation for the histogram based on the measure of leak.

40. The apparatus of claim 23 wherein the controller is configured to determine a measure of ventilation stability and to distinguish the measures of ventilation for the histogram based on the measure of stability.

41. The apparatus of claim 40 wherein the controller determines the measure of ventilation stability by detecting any of one or more of an awake period, an apnea event, a periodic breathing event and an arousal event.

42. The apparatus of claim 23 wherein the controller is configured to process data representing the histogram to generate a hyperventilation indicator, the indicator representing an occurrence of an event of hyperventilation.

43. The ventilation assessment apparatus of claim 23 wherein the controller is configured to change an operational parameter of a respiratory treatment apparatus assisting the patient's respiration based on the evaluation of the histogram.

44. A ventilation assessment apparatus comprising:
a flow sensor configured to measure a flow of breathable gas, and
a controller having at least one processor to access data representing a measured flow of breathable gas attributable to patient respiration obtained from the flow sensor, the controller being further configured to (a) control measuring of the flow of breathable gas with the flow sensor, (b) derive measures of ventilation from the measure of flow, (c) determine a histogram of the measures of ventilation, wherein the measures are volumes of breathable gas measured over a time interval and (d) evaluate the histogram in the processor and, based on the evaluation, output an indication of occurrence of hyperventilation, wherein the controller is configured to:
process data associated with the histogram to calculate a skewness index;
compare the skewness index to a threshold; and
indicate an occurrence of hyperventilation based on the comparison.

45. A ventilation assessment system comprising:
means for measuring a flow of breathable gas attributable to patient respiration during a treatment session,
means for deriving measures of ventilation from the measure of flow,
means for determining a histogram with the measures of ventilation,
wherein the measures are volumes of breathable gas measured over a time interval, and
means for evaluating the histogram in a processor and, based on the evaluation, outputting an indication of occurrence of hypoventilation.

46. The system of claim 45 further comprising means for displaying a visual graph of the histogram.

47. The system of claim 45 further comprising means for evaluating a skewness index based on data associated with the histogram to detect an occurrence of hypoventilation or hyperventilation.

48. The system of claim 45 further comprising means for evaluating a number of histogram peaks from data associated with the histogram to detect an occurrence of hypoventilation.

49. The system of claim 45 further comprising means for evaluating a kurtosis index based on data associated with the histogram to detect a presence or absence of hypoventilation.

50. The system of claim 45 further comprising means for generating a breathable gas for a patient at a pressure above atmospheric pressure based on an assessment of any one or more of (a) the histogram, (b) a number of peaks of the histogram, (c) a kurtosis index determined from data associated with the histogram and (d) a skewness index determined from data associated with the histogram.

51. The system of claim 45 further comprising means for processing data representing the histogram to generate a hypoventilation indicator, the indicator representing an occurrence of an event of hypoventilation.

52. The system of claim 51 wherein the hypoventilation indicator comprises a probability value.

53. The system of claim 51 wherein further comprising means for detecting peaks of the histogram.

54. The system of claim 53 further comprising means for calculating a distance between peaks of the histogram and transforming the distance into a probability space.

55. The system of claim 45 further comprising means for calculating a gradient between peaks of the histogram.

56. The system of claim 55 further comprising means for calculating an area with respect to the gradient and transforming the area into a probability space.

57. The system of claim 45 further comprising means for calculating a set of features of the histogram and generating indication based on an evaluation of the set of features.

58. The system of claim 57 wherein the set of features comprises two or more of the following features: a gradient between two largest peaks, a gradient between a largest peak and a center point, a gradient between a second largest peak and a center point, an area between two largest peaks, an area between a largest peak and a center point, an area between a second largest peak and a center point, a shape feature, kurtosis value and skewness value.

59. The system of claim 45 further comprising a leak detector to determine a measure of leak, wherein the system is configured to distinguish the measures of ventilation for the histogram based on the measure of leak.

60. The system of claim 45 further comprising a ventilation stability detector, wherein the system is configured to distinguish the measures of ventilation for the histogram based on the measure of stability.

61. The system of claim 60 wherein the ventilation stability detector includes means for detecting one or more of an awake period, an apnea event, a periodic breathing event an arousal event.

62. The ventilation assessment system of claim 45 further comprising means for changing an operational parameter of a respiratory treatment apparatus assisting the patient's respiration based on the evaluating of the histogram.

* * * * *